United States Patent
Honold et al.

(10) Patent No.: US 7,618,964 B2
(45) Date of Patent: Nov. 17, 2009

(54) BENZAMIDE DERIVATIVES, THEIR MANUFACTURE AND USE AS PHARMACEUTICAL AGENTS

(75) Inventors: Konrad Honold, Penzberg (DE); Klaus Kaluza, Bad Heilbrunn (DE); Birgit Masjost, Basel (CH); Wolfgang Schaefer, Mannheim (DE); Stefan Scheiblich, Penzberg (DE)

(73) Assignee: Hoffmann-La Roche Inc., Nutley, NJ (US)

(*) Notice: Subject to any disclaimer, the term of this patent is extended or adjusted under 35 U.S.C. 154(b) by 89 days.

(21) Appl. No.: 11/793,751

(22) PCT Filed: Dec. 22, 2005

(86) PCT No.: PCT/EP2005/013850
§ 371 (c)(1),
(2), (4) Date: Jun. 20, 2007

(87) PCT Pub. No.: WO2006/066913
PCT Pub. Date: Jun. 29, 2006

(65) Prior Publication Data
US 2008/0039460 A1 Feb. 14, 2008

(30) Foreign Application Priority Data
Dec. 23, 2004 (EP) ................... 04030622

(51) Int. Cl.
*A61K 31/5377* (2006.01)
*A61K 31/44* (2006.01)
*C07D 413/14* (2006.01)
*C07D 471/02* (2006.01)

(52) U.S. Cl. .............. 514/234.2; 514/303; 514/333; 544/127; 546/118; 546/256

(58) Field of Classification Search ............... 544/127; 546/118, 256; 514/234.2, 303, 333
See application file for complete search history.

(56) References Cited

U.S. PATENT DOCUMENTS 7,256,287 B2 * 8/2007 Sircar et al. ............ 544/235
2004/0242883 A1 12/2004 Boschelli et al.

FOREIGN PATENT DOCUMENTS

| WO | WO 01/00213 | 1/2001 |
|---|---|---|
| WO | WO 01/47922 | 7/2001 |
| WO | WO 03/035065 | 5/2003 |
| WO | WO 2004/024897 | 3/2004 |
| WO | WO 2005/063746 | 7/2005 |
| WO | WO 2005/063747 | 7/2005 |
| WO | WO 2006/066914 | 9/2006 |

OTHER PUBLICATIONS

Golub et al. Science (1999), vol. 286 521-537.*
Lala et al. Cancer and Metastasis Reviews (1998), 17(1), 91-106.*
Sawyer et al., Expert Opin. Investig. Drugs 10 (2001) pp. 1327-1344.
Misbach et al., Bone 24 (1999) pp. 437-449.

* cited by examiner

*Primary Examiner*—Kamal A Saeed
*Assistant Examiner*—Samantha L Shterengarts
(74) *Attorney, Agent, or Firm*—George W. Johnston; Patricia S. Rocha-Tramaloni; Gene J. Yao

(57) ABSTRACT

Objects of the present invention are the compounds of formula I

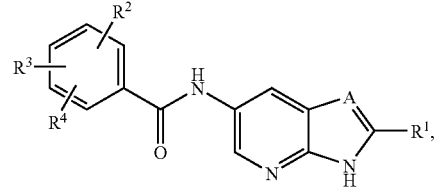

their pharmaceutically acceptable salts, enantiomeric forms, diastereoisomers and racemates, the preparation of the above-mentioned compounds, medicaments containing them and their manufacture, as well as the use of the above-mentioned compounds in the control or prevention of illnesses such as cancer.

11 Claims, No Drawings

US 7,618,964 B2

BENZAMIDE DERIVATIVES, THEIR MANUFACTURE AND USE AS PHARMACEUTICAL AGENTS

This invention relates to benzamide derivatives that inhibit the activity of protein kinases, to a process for their manufacture, pharmaceutical compositions containing them and their manufacture as well as the use of these compounds as pharmaceutically active agents.

BACKGROUND OF THE INVENTION

Protein kinases are enzymes that catalyze the transfer of a phosphate group from ATP to an amino acid residue, such as tyrosine, serine, threonine, or histidine on a protein. Regulation of these protein kinases is essential for the control of a wide variety of cellular events including proliferation and migration.

Inappropriate activation of tyrosine kinases is known to be involved in a variety of disease states including inflammatory, immunological, CNS disorders, or oncological disorders, or bone diseases. See for example Susva, M., et al., Trends Pharmacol. Sci. 21 (2000) 489-495; Biscardi, J. S., et al., Adv. Cancer Res. 76 (2000) 61-119.

The tyrosine kinases are a class of protein kinases. The Src family which consists of at least eight members (Src, Fyn, Lyn, Yes, Lck, Fgr, Hck and Blk) that participate in a variety of signaling pathways represents the major family of cytoplasmic protein tyrosine kinases (Schwartzberg, P. L., Oncogene 17 (1998) 1463-1468). The prototypical member of this tyrosine kinase family is Src, which is involved in proliferation and migration responses in many cell types (Sawyer, T., et al., Expert Opin. Investig. Drugs 10 (2001) 1327-1344). Src activity has been shown to be elevated in different cancers, e.g. breast, colon (>90%), pancreatic (>90%) and liver (>90%) tumors. Highly increased Src activity is also associated with metastasis (>90%) and poor prognosis. Antisense Src message impedes growth of colon tumor cells in nude mice (Staley, C. A., Cell Growth Differ. 8 (1997) 269-274), suggesting that Src inhibitors could slow tumor growth. Furthermore, in addition to its role in cell proliferation, Src also acts in stress response pathways, including the hypoxia response. Nude mice studies with colon tumor cells expressing antisense Src message have reduced vascularization (Ellis, L. M., et al., J. Biol. Chem. 273 (1998) 1052-1057), which suggests that Src inhibitors could be anti-angiogenic as well as anti-proliferative.

Src disrupts E-cadherin associated cell-cell interactions (Avizienyte, E., et al., Nature Cell Bio. 4 (2002) 632-638). A low molecular weight Src inhibitor prevents this disruption thereby reducing cancer cell metastasis (Nam, J. S., et al., Clin. Cancer Res. 8 (2002) 2430-2436).

Src inhibitors may prevent the secondary injury that results from a VEGF-mediated increase in vascular permeability such as that seen following stroke (Eliceiri, B. P., et al., Mol. Cell. 4 (1999) 915-924; Paul, R., et al., Nat. Med. 7 (2001) 222-227).

Blockade of Src prevents dissociation of the complex involving Flk, VE-cadherin, and β-catenin with the same kinetics with which it prevents VEGF-mediated VP/edema and account for the Src requirement in VEGF-mediated permeability and provide a basis for Src inhibition as a therapeutic option for patients with acute myocardial infarction (Weis, S., et al., J. Clin. Invest. 113 (2004) 885-894).

Src also plays a role in osteoporosis. Mice genetically engineered to be deficient in Src production were found to exhibit osteopetrosis, the failure to resorb bone (Soriano, P., et al., Cell 64 (1991) 693-702; Boyce, B. F., et al., J. Clin., Invest. 90 (1992) 1622-1627). This defect was characterized by a lack of osteoclast activity. Since osteoclasts normally express high levels of Src, inhibition of Src kinase activity may be useful in the treatment of osteoporosis (Missbach, M., et al., Bone 24 (1999) 437-449).

Low molecular weight inhibitors for protein kinases are widely known in the state of the art. For src inhibition such inhibitors are based on i.e. thieno-pyridine derivatives (US 2004/0242883); pyrido-pyrimidine derivatives (WO 04/085436); pyrido-pyrimidone derivatives (WO 04/041823); pyrimidine derivatives (WO 03/004492 and WO 01/00213); Quinazoline derivatives (WO 01/94341 and WO 02/016352); isoxazole derivatives (WO 02/083668) and pyrazole derivatives (WO 02/092573).

Some phenyl-aza-benzimidazoles are known as inhibitors of IgE-mediated immune response and suppressors of cytokines and leukocytes with antiproliferative effect from WO 04/024897. And some benzimidazole-pyrazoles and -indazoles are known as kinase inhibitors from WO 03/035065, especially as inhibitors against Kdr, Syk and Itk tyrosine kinases.

SUMMARY OF THE INVENTION

The present invention relates to benzamide derivatives of the general formula I

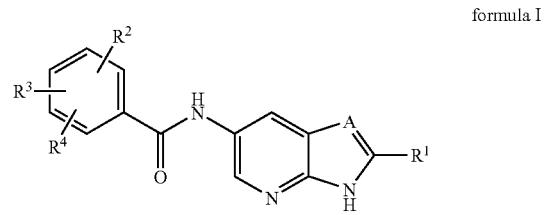

formula I wherein,
R$^1$ is a phenyl group optionally substituted with halogen, cyano, nitro, amino, —C(O)OH, heterocyclyl, —O-heterocyclyl, —S(O)$_2$NH$_2$, —X-alkyl or —Y-cycloalkyl;
or a heteroaryl group optionally substituted with halogen, nitro, amino, heterocyclyl or —Z-alkyl;
and all alkyl groups are optionally substituted one or several times by halogen, hydroxy, alkoxy, amino, alkylamino, dialkylamino or alkylsulfonyl;
X is a single bond, —NR—, —O—, —S—, —CH$_2$—S(O)$_2$ NH—, —NHS(O)$_2$—, —S(O)$_2$NH—, —S(O)$_2$—, —S(O)—, —NRC(O)— or —C(O)NR—;
Y is —NRC(O)— or —C(O)NR—;
Z is a single bond, —NR— or —O—;
R is hydrogen or alkyl, wherein the alkyl is optionally substituted one or several times by halogen or alkoxy;
R$^2$, R$^3$ and R$^4$ independently represent hydrogen, halogen, cyano, nitro, amino, hydroxy, amino, alkoxy, alkylamino, dialkylamino, alkyl, wherein the alkyl and alkoxy groups are optionally substituted one or several times by halogen;
A is =CH— or =N—;
and all pharmaceutically acceptable salts thereof.

The compounds according to this invention show activity as protein kinase inhibitors, in particular Src family tyrosine kinase inhibitors, and may therefore be useful for the treatment of diseases mediated by said tyrosine kinases.

Src family tyrosine kinases are known to be involved in a variety of disease states. Compounds of the present invention may be used as active agents in the prevention and therapy of, for example, transplant rejection, inflammatory bowel syndrome, rheumatoid arthritis, psoriasis, restenosis, allergic asthma, Alzheimer's disease, Parkinson, stroke, osteoporosis, benign hyperplasias and cancer including colon, breast, lung and pancreatic cancer and leukemia.

Objects of the present invention are the compounds of formula I and pharmaceutically acceptable salts and their enantiomeric forms, the preparation of the above-mentioned compounds, medicaments containing them and their manufacture as well as the use of the above-mentioned compounds in the control or prevention of illnesses, especially of illnesses and disorders as mentioned above or in the manufacture of corresponding medicaments.

DETAILED DESCRIPTION OF THE INVENTION

As used herein, the term "alkyl" means a saturated, straight-chain or branched-chain hydrocarbon containing from 1 to 4, preferably 1 or 2, carbon atoms, such as methyl, ethyl, n-propyl, isopropyl, n-butyl, 2-butyl, t-butyl.

As used herein, the term "alkoxy" means an alkyl group as defined above which is connected via an oxygen (—O—) atom.

If said alkyl or alkoxy group is substituted one or several times by halogen, it is preferably substituted by fluorine or chlorine, especially fluorine. Examples are difluoromethyl, trifluoromethyl, 2,2,2-trifluoroethyl, perfluorethyl, difluoromethoxy, trifluoromethoxy, 2,2,2-trifluoroethoxy, perfluoroethoxy and the like, especially trifluoromethyl and trifluoromethoxy.

The term "halogen" as used herein means fluorine, chlorine, bromine and iodine, preferably fluorine, chlorine or bromine and more preferred fluorine and chlorine.

The term "halogen" as used in definition of $R^1$ is preferably fluorine. The term "halogen" as used in definition of $R^2$ is preferably chlorine or bromine, more preferably chlorine.

The term "heteroaryl" means a mono- or bicyclic aromatic ring selected from pyridyl, thienyl, benzimidazolyl, pyrimidyl, thiazolyl, quinolyl, pyridazinyl, pyrazinyl, oxazolyl, quinazolinyl, indolyl, benzothiophenyl or benzofuranyl, especially from pyridyl, thienyl, benzimidazolyl, pyrimidyl, thiazolyl, quinolyl or pyridazinyl, and more preferred from pyridyl, thienyl or benzimidazolyl.

The term "heterocyclyl" means a saturated, monocyclic hydrocarbon ring with 5 to 6 ring atoms which contains up to 3, preferably 1 or 2 heteroatoms selected independently from N, O or S and the remaining ring atoms being carbon atoms. Such saturated heterocyclic group can be optionally substituted one to three, preferably one or two times by alkyl, which is defined as above, preferably by methyl. Examples of such saturated heterocyclic groups are pyrrolidinyl, morpholinyl, piperazinyl, N-methyl-piperazinyl, piperidyl and the like, preferably morpholinyl and N-methyl-piperazinyl.

If $R^1$ is phenyl, said phenyl is optionally substituted one or several times, preferably one or two times, at the ortho, meta or para position.

If $R^1$ is heteroaryl, said heteroaryl is optionally substituted one or several times, preferably one or two times.

The compounds of formula I can exist in different tautomeric forms and in variable mixtures thereof. All tautomeric forms of the compounds of formula I and mixtures thereof are an objective of the invention. For example, if A in the definition of formula is =N—, the imidazole part of pyridyl-imidazole ring system of formula I can exist in two tautomeric forms as shown here below:

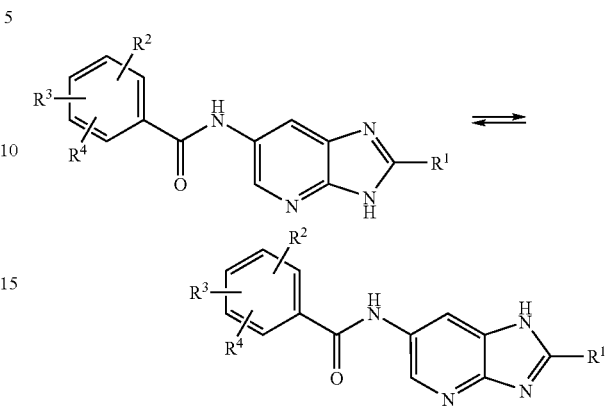

(if A is =N—)

An embodiment of the invention are the compounds according to formula I, wherein
  $R^1$ is a phenyl group optionally substituted with halogen, cyano, nitro, amino, —C(O)OH, heterocyclyl, —S(O)$_2$NH$_2$ or —X-alkyl;
    or a heteroaryl group optionally substituted with halogen, nitro, amino or —Z-alkyl;
    and all alkyl groups are optionally substituted one or several times by halogen, hydroxy, alkoxy, amino, alkylamino or dialkylamino.

Another embodiment of the invention are the compounds according to formula I, wherein
  $R^1$ is a phenyl group optionally substituted with halogen, cyano, nitro, amino, —C(O)OH, heterocyclyl, —S(O)$_2$NH$_2$ or —X-alkyl;
    or a heteroaryl group optionally substituted with halogen, nitro, amino or —Z-alkyl;
    and all alkyl groups are optionally substituted one or several times by halogen, hydroxy, alkoxy, amino, alkylamino or dialkylamino; and
  $R^4$ is hydrogen.

Another embodiment of the invention are the compounds according to formula I, wherein
  $R^4$ is hydrogen.

Another embodiment of the invention are the compounds according to formula I, wherein
  A is =N—.

Another embodiment of the invention are the compounds according to formula I, wherein
  $R^4$ is hydrogen; and
  A is =N—.

An embodiment of the invention are the compounds according to formula I, wherein
  $R^1$ is a phenyl group optionally substituted with halogen, cyano, nitro, amino, —C(O)OH, heterocyclyl, —S(O)$_2$NH$_2$ or —X-alkyl;
    wherein the alkyl group is optionally substituted one or several times by halogen, hydroxy, alkoxy, amino, alkylamino or dialkylamino.

An embodiment of the invention are the compounds according to formula I, wherein
  $R^1$ is a phenyl group optionally substituted with halogen, cyano, nitro, amino, —C(O)OH, heterocyclyl, —S(O)$_2$NH$_2$ or —X-alkyl;

wherein the alkyl group is optionally substituted one or several times by halogen, hydroxy, alkoxy, amino, alkylamino or dialkylamino; and $R^4$ is hydrogen.

Another embodiment of the invention are the compounds according to formula I, wherein $R^1$ is a phenyl group optionally substituted with halogen, cyano, nitro, amino, —C(O)OH, heterocyclyl, —S(O)$_2$NH$_2$ or —X-alkyl;

wherein the alkyl group is optionally substituted one or several times by halogen, hydroxy, alkoxy, amino, alkylamino or dialkylamino; and A is =N—.

Another embodiment of the invention are the compounds according to formula I, wherein $R^1$ is a phenyl group optionally substituted with halogen, cyano, nitro, amino, —C(O)OH, heterocyclyl, —S(O)$_2$NH$_2$ or —X-alkyl;

wherein the alkyl group is optionally substituted one or several times by halogen, hydroxy, alkoxy, amino, alkylamino or dialkylamino;

$R^4$ is hydrogen; and

A is =N—.

An embodiment of the invention are the compounds according to formula I, wherein $R^1$ is a phenyl group.

An embodiment of the invention are the compounds according to formula I, wherein $R^1$ is a phenyl group; and $R^4$ is hydrogen.

Another embodiment of the invention are the compounds according to formula I, wherein $R^1$ is a phenyl group; and A is =N—.

Another embodiment of the invention are the compounds according to formula I, wherein $R^1$ is a phenyl group;

$R^4$ is hydrogen; and

A is =N—.

Such compounds, for example, may be selected from the group consisting of:

N-(2-Phenyl-3H-imidazo[4,5-b]pyridin-6-yl)-benzamide;
2-Chloro-N-(2-phenyl-3H-imidazo[4,5-b]pyridin-6-yl)-benzamide;
2-Chloro-6-methyl-N-(2-phenyl-3H-imidazo[4,5-b]pyridin-6-yl)-benzamide;
2-Bromo-N-(2-phenyl-3H-imidazo[4,5-b]pyridin-6-yl)-benzamide;
2-Chloro-5-nitro-N-(2-phenyl-3H-imidazo[4,5-b]pyridin-6-yl)-benzamide;
5-Amino-2-chloro-N-(2-phenyl-3H-imidazo[4,5-b]pyridin-6-yl)-benzamide;
2-Methyl-5-nitro-N-(2-phenyl-3H-imidazo[4,5-b]pyridin-6-yl)-benzamide; and
5-Amino-2-methyl-N-(2-phenyl-3H-imidazo[4,5-b]pyridin-6-yl)-benzamide.

An embodiment of the invention are the compounds according to formula I, wherein $R^1$ is a phenyl group optionally substituted with halogen, cyano, nitro, amino, —C(O)OH or —S(O)$_2$NH$_2$.

An embodiment of the invention are the compounds according to formula I, wherein $R^1$ is a phenyl group optionally substituted with halogen, cyano, nitro, amino, —C(O)OH or —S(O)$_2$NH$_2$; and $R^4$ is hydrogen.

Another embodiment of the invention are the compounds according to formula I, wherein $R^1$ is a phenyl group optionally substituted with halogen, cyano, nitro, amino, —C(O)OH or —S(O)$_2$NH$_2$; and A is =N—.

Another embodiment of the invention are the compounds according to formula I, wherein $R^1$ is a phenyl group optionally substituted with halogen, cyano, nitro, amino, —C(O)OH or —S(O)$_2$NH$_2$;

$R^4$ is hydrogen; and

A is =N—.

Such compounds, for example, may be selected from the group consisting of:

2-Chloro-N-[2-(4-sulfamoyl-phenyl)-3H-imidazo[4,5-b]pyridin-6-yl]-benzamide;
2-Chloro-N-[2-(4-nitro-phenyl)-3H-imidazo[4,5-b]pyridin-6-yl]-benzamide;
2-Chloro-N-[2-(3-nitro-phenyl)-3H-imidazo[4,5-b]pyridin-6-yl]-benzamide
N-[2-(3-Amino-phenyl)-3H-imidazo[4,5-b]pyridin-6-yl]-2-chloro-benzamide; and
3-[6-(2-Chloro-benzoylamino)-3H-imidazo[4,5-b]pyridin-2-yl]-benzoic acid.

An embodiment of the invention are the compounds according to formula I, wherein $R^1$ is a phenyl group substituted with heterocyclyl.

An embodiment of the invention are the compounds according to formula I, wherein $R^1$ is a phenyl group substituted with heterocyclyl; and $R^4$ is hydrogen.

Another embodiment of the invention are the compounds according to formula I, wherein $R^1$ is a phenyl group substituted with heterocyclyl; and A is =N—.

Another embodiment of the invention are the compounds according to formula I, wherein $R^1$ is a phenyl group substituted with heterocyclyl;

$R^4$ is hydrogen; and

A is =N—.

Such a compound is for example:

2-Chloro-N-[2-(4-morpholin-4-yl-phenyl)-3H-imidazo[4,5-b]pyridin-6-yl]-benzamide.

An embodiment of the invention are the compounds according to formula I, wherein $R^1$ is a phenyl group optionally substituted with —X-alkyl;

wherein the alkyl group is optionally substituted one or several times by halogen, hydroxy, alkoxy, amino, alkylamino or dialkylamino.

An embodiment of the invention are the compounds according to formula I, wherein $R^1$ is a phenyl group optionally substituted with —X-alkyl;

wherein the alkyl group is optionally substituted one or several times by halogen, hydroxy, alkoxy, amino, alkylamino or dialkylamino; and $R^4$ is hydrogen.

Another embodiment of the invention are the compounds according to formula I, wherein $R^1$ is a phenyl group optionally substituted with —X-alkyl;

wherein the alkyl group is optionally substituted one or several times by halogen, hydroxy, alkoxy, amino, alkylamino or dialkylamino; and A is =N—.

Another embodiment of the invention are the compounds according to formula I, wherein
- $R^1$ is a phenyl group optionally substituted with —X-alkyl;
  wherein the alkyl group is optionally substituted one or several times by halogen, hydroxy, alkoxy, amino, alkylamino or dialkylamino;
- $R^4$ is hydrogen; and
- A is =N—.

Another embodiment of the invention are the compounds according to formula I, wherein
- $R^1$ is a phenyl group optionally substituted with —X-alkyl;
  wherein the alkyl group is optionally substituted one or several times by halogen, hydroxy, alkoxy, amino, alkylamino or dialkylamino; and
- X is a single bond, —NR—, —O—, —S—, —CH$_2$—S(O)$_2$NH—, —NHS(O)$_2$—, —S(O)$_2$NH—, —S(O)$_2$—, —S(O)—.

Another embodiment of the invention are the compounds according to formula I, wherein
- $R^1$ is a phenyl group optionally substituted with —X-alkyl;
  wherein the alkyl group is optionally substituted one or several times by halogen, hydroxy, alkoxy, amino, alkylamino or dialkylamino;
- X is a single bond, —NR—, —O—, —S—, —CH$_2$—S(O)$_2$NH—, —NHS(O)$_2$—, —S(O)$_2$NH—, —S(O)$_2$—, —S(O)—;
- $R^4$ is hydrogen; and
- A is =N—.

Another embodiment of the invention are the compounds according to formula I, wherein
- $R^1$ is a phenyl group optionally substituted with —X-alkyl;
  wherein the alkyl group is optionally substituted one or several times by halogen, hydroxy, alkoxy, amino, alkylamino or dialkylamino;
- X is a single bond, —NR—, —O— or, —S—;
- $R^4$ is hydrogen; and
- A is =N—.

Such compounds, for example, may be selected from the group consisting of:
2-Chloro-N-{2-[4-(2-methoxy-ethoxy)-phenyl]-3H-imidazo[4,5-b]pyridin-6-yl}-benzamide;
2-Chloro-N-{2-[3-(2-methoxy-ethoxy)-phenyl]-3H-imidazo[4,5-b]pyridin-6-yl}-benzamide;
2-Chloro-N-{2-[4-(2-diethylamino-ethoxy)-phenyl]-3H-imidazo[4,5-b]pyridin-6-yl}-benzamide;
2-Chloro-N-{2-[4-(2-diethylamino-ethoxy)-phenyl]-3H-imidazo[4,5-b]pyridin-6-yl}-benzamide; acetic acid salt;
2-Chloro-N-[2-(3-methylsulfanyl-phenyl)-3H-imidazo[4,5-b]pyridin-6-yl]-benzamide; and
2-Chloro-N-[2-(4-methylsulfanyl-phenyl)-3H-imidazo[4,5-b]pyridin-6-yl]-benzamide.

Another embodiment of the invention are the compounds according to formula I, wherein
- $R^1$ is a phenyl group optionally substituted with —X-alkyl;
  wherein the alkyl group is optionally substituted one or several times by halogen, hydroxy, alkoxy, amino, alkylamino or dialkylamino; and
- X is —CH$_2$—S(O)$_2$NH—, —NHS(O)$_2$—, —S(O)$_2$NH—, —S(O)$_2$— or —S(O)—.

Another embodiment of the invention are the compounds according to formula I, wherein
- $R^1$ is a phenyl group optionally substituted with —X-alkyl;
  wherein the alkyl group is optionally substituted one or several times by halogen, hydroxy, alkoxy, amino, alkylamino or dialkylamino;
- X is —CH$_2$—S(O)$_2$NH—, —NHS(O)$_2$—, —S(O)$_2$NH—, —S(O)$_2$— or —S(O)—;
- $R^4$ is hydrogen; and
- A is =N—.

Such a compound is for example:
2-Chloro-N-[2-(3-methanesulfinyl-phenyl)-3H-imidazo[4,5-b]pyridin-6-yl]-benzamide.

Another embodiment of the invention are the compounds according to formula I, wherein
- $R^1$ is a phenyl group optionally substituted with —X-alkyl;
  wherein the alkyl group is optionally substituted one or several times by halogen, hydroxy, alkoxy, amino, alkylamino or dialkylamino; and
- X is —NRC(O)— or —C(O)NR—.

Another embodiment of the invention are the compounds according to formula I, wherein
- $R^1$ is a phenyl group optionally substituted with —X-alkyl;
  wherein the alkyl group is optionally substituted one or several times by halogen, hydroxy, alkoxy, amino, alkylamino or dialkylamino;
- X is —NRC(O)— or —C(O)NR—;
- $R^4$ is hydrogen; and
- A is =N—.

Such a compound is for example:
N-[2-(3-Acetylamino-phenyl)-3H-imidazo[4,5-b]pyridin-6-yl]-2-chloro-benzamide;
3-(6-(2-chlorobenzoylamino)-3H-imidazo[4,5-b]pyridin-2-yl)-N-(3-methoxy-propyl)-benzamide; and
3-(6-(2-chlorobenzoylamino)-3H-imidazo[4,5-b]pyridin-2-yl)-N-isopropyl-benzamide.

An embodiment of the invention are the compounds according to formula I, wherein
- $R^1$ is a heteroaryl group optionally substituted with halogen, nitro, amino or —Z-alkyl;
  wherein the alkyl group is optionally substituted one or several times by halogen, hydroxy, alkoxy, amino, alkylamino or dialkylamino.

An embodiment of the invention are the compounds according to formula I, wherein
- $R^1$ is a heteroaryl group optionally substituted with halogen, nitro, amino or —Z-alkyl;
  wherein the alkyl group is optionally substituted one or several times by halogen, hydroxy, alkoxy, amino, alkylamino or dialkylamino; and
- $R^4$ is hydrogen.

Another embodiment of the invention are the compounds according to formula I, wherein
- $R^1$ is a heteroaryl group optionally substituted with halogen, nitro, amino or —Z-alkyl;
  wherein the alkyl group is optionally substituted one or several times by halogen, hydroxy, alkoxy, amino, alkylamino or dialkylamino; and
- A is =N—.

Another embodiment of the invention are the compounds according to formula I, wherein
- $R^1$ is a heteroaryl group optionally substituted with halogen, nitro, amino or —Z-alkyl;
  wherein the alkyl group is optionally substituted one or several times by halogen, hydroxy, alkoxy, amino, alkylamino or dialkylamino;
- $R^4$ is hydrogen; and
- A is =N—.

An embodiment of the invention are the compounds according to formula I, wherein
- $R^1$ is a pyridyl, thienyl or benzimidazolyl group optionally substituted with halogen, nitro, amino, heterocyclyl or —Z-alkyl;

wherein the alkyl group is optionally substituted one or several times by halogen, hydroxy, alkoxy, amino, alkylamino or dialkylamino.

An embodiment of the invention are the compounds according to formula I, wherein
$R^1$ is a pyridyl, thienyl or benzimidazolyl group optionally substituted with halogen, nitro, amino, heterocyclyl or —Z-alkyl;
wherein the alkyl group is optionally substituted one or several times by halogen, hydroxy, alkoxy, amino, alkylamino or dialkylamino; and
$R^4$ is hydrogen.

Another embodiment of the invention are the compounds according to formula I, wherein
$R^1$ is a pyridyl, thienyl or benzimidazolyl group optionally substituted with halogen, nitro, amino, heterocyclyl or —Z-alkyl;
wherein the alkyl group is optionally substituted one or several times by halogen, hydroxy, alkoxy, amino, alkylamino or dialkylamino; and
A is =N—.

Another embodiment of the invention are the compounds according to formula I, wherein
$R^1$ is a pyridyl, thienyl or benzimidazolyl group optionally substituted with halogen, nitro, amino, heterocyclyl or —Z-alkyl;
wherein the alkyl group is optionally substituted one or several times by halogen, hydroxy, alkoxy, amino, alkylamino or dialkylamino;
$R^4$ is hydrogen; and
A is =N—.

An embodiment of the invention are the compounds according to formula I, wherein
$R^1$ is a pyridyl group optionally substituted with halogen, nitro, amino, —Z-alkyl;
wherein the alkyl group is optionally substituted one or several times by halogen, hydroxy, alkoxy, amino, alkylamino or dialkylamino.

An embodiment of the invention are the compounds according to formula I, wherein
$R^1$ is a pyridyl group optionally substituted with halogen, nitro, amino, —Z-alkyl;
wherein the alkyl group is optionally substituted one or several times by halogen, hydroxy, alkoxy, amino, alkylamino or dialkylamino; and
$R^4$ is hydrogen.

Another embodiment of the invention are the compounds according to formula I, wherein
$R^1$ is a pyridyl group optionally substituted with halogen, nitro, amino, —Z-alkyl;
wherein the alkyl group is optionally substituted one or several times by halogen, hydroxy, alkoxy, amino, alkylamino or dialkylamino; and
A is =N—.

Another embodiment of the invention are the compounds according to formula I, wherein
$R^1$ is a pyridyl group optionally substituted with halogen, nitro, amino, —Z-alkyl;
wherein the alkyl group is optionally substituted one or several times by halogen, hydroxy, alkoxy, amino, alkylamino or dialkylamino;
$R^4$ is hydrogen; and
A is =N—.

Such compounds, for example, may be selected from the group consisting of:
2-Chloro-N-[2-(6-methyl-pyridin-3-yl)-3H-imidazo[4,5-b]pyridin-6-yl]-benzamide; and
2-Chloro-N-[2-(2-methyl-pyridin-4-yl)-3H-imidazo[4,5-b]pyridin-6-yl]-benzamide.

An embodiment of the invention are the compounds according to formula I, wherein
$R^1$ is a thienyl or benzimidazolyl group optionally substituted with —Z-alkyl;
Z is a single bond.

An embodiment of the invention are the compounds according to formula I, wherein
$R^1$ is a thienyl or benzimidazolyl group optionally substituted with —Z-alkyl;
Z is a single bond; and
$R^4$ is hydrogen.

Another embodiment of the invention are the compounds according to formula I, wherein
$R^1$ is a thienyl or benzimidazolyl group optionally substituted with —Z-alkyl;
Z is a single bond; and
A is =N—.

Another embodiment of the invention are the compounds according to formula I, wherein
$R^1$ is a thienyl or benzimidazolyl group optionally substituted with —Z-alkyl;
Z is a single bond;
$R^4$ is hydrogen; and
A is =N—.

Such compounds, for example, may be selected from the group consisting of:
N-[2-(1H-Benzoimidazol-5-yl)-3H-imidazo[4,5-b]pyridin-6-yl]-2-chloro-benzamide;
2-Chloro-N-(2-thiophen-2-yl-3H-imidazo[4,5-b]pyridin-6-yl)-benzamide; and
2-Chloro-N-(2-thiophen-3-yl-3H-imidazo[4,5-b]pyridin-6-yl)-benzamide.

Another embodiment of the invention are the compounds according to formula I, wherein
$R^4$ is hydrogen; and
A is =CH—.

Another embodiment of the invention are the compounds according to formula I, wherein
$R^1$ is a phenyl group optionally substituted with halogen, cyano, nitro, amino, —C(O)OH, heterocyclyl, —S(O)$_2$NH$_2$ or —X-alkyl;
wherein the alkyl group is optionally substituted one or several times by halogen, hydroxy, alkoxy, amino, alkylamino or dialkylamino;
$R^4$ is hydrogen; and
A is =CH—.

Another embodiment of the invention are the compounds according to formula I, wherein
$R^1$ is a phenyl group;
$R^4$ is hydrogen; and
A is =CH—.

Such compounds, for example, may be selected from the group consisting of:
2-Chloro-N-(2-phenyl-1H-pyrrolo[2,3-b]pyridin-5-yl)-benzamide;
2-Methyl-N-(2-phenyl-1H-pyrrolo[2,3-b]pyridin-5-yl)-benzamide;
2-Methoxy-N-(2-phenyl-1H-pyrrolo[2,3-b]pyridin-5-yl)-benzamide;
2,4-Dichloro-N-(2-phenyl-1H-pyrrolo[2,3-b]pyridin-5-yl)-benzamide
2-Chloro-6-methyl-N-(2-phenyl-1H-pyrrolo[2,3-b]pyridin-5-yl)-benzamide; and
3,5-Dimethoxy-N-(2-phenyl-1H-pyrrolo[2,3-b]pyridin-5-yl)-benzamide.

Another embodiment of the invention are the compounds according to formula I, wherein
- $R^1$ is a phenyl group optionally substituted with halogen, cyano, nitro, amino, —C(O)OH or —S(O)$_2$NH$_2$;
- $R^4$ is hydrogen; and
- A is =CH—.

Another embodiment of the invention are the compounds according to formula I, wherein
- $R^1$ is a phenyl group substituted with heterocyclyl;
- $R^4$ is hydrogen; and
- A is =CH—.

Another embodiment of the invention are the compounds according to formula I, wherein
- $R^1$ is a phenyl group optionally substituted with —X-alkyl;
  - wherein the alkyl group is optionally substituted one or several times by halogen, hydroxy, alkoxy, amino, alkylamino or dialkylamino;
- $R^4$ is hydrogen; and
- A is =CH—.

Another embodiment of the invention are the compounds according to formula I, wherein
- $R^1$ is a phenyl group optionally substituted with —X-alkyl;
  - wherein the alkyl group is optionally substituted one or several times by halogen, hydroxy, alkoxy, amino, alkylamino or dialkylamino;
- X is a single bond, —NR—, —O—, —S—, —CH$_2$—S(O)$_2$ NH—, —NHS(O)$_2$—, —S(O)$_2$NH—, —S(O)$_2$—, —S(O)—;
- $R^4$ is hydrogen; and
- A is =CH—.

Another embodiment of the invention are the compounds according to formula I, wherein
- $R^1$ is a phenyl group optionally substituted with —X-alkyl;
  - wherein the alkyl group is optionally substituted one or several times by halogen, hydroxy, alkoxy, amino, alkylamino or dialkylamino;
- X is a single bond, —NR—, —O— or, —S—;
- $R^4$ is hydrogen; and
- A is =CH—.

Such compounds, for example, may be selected from the group consisting of:
N-{2-[3-(2-Methoxy-ethoxy)-phenyl]-1H-pyrrolo[2,3-b]pyridin-5-yl}-2-methyl-benzamide;
3,5-Dimethoxy-N-{2-[3-(2-methoxy-ethoxy)-phenyl]-1H-pyrrolo[2,3-b]pyridin-5-yl}-benzamide;
4-Methoxy-N-{2-[3-(2-methoxy-ethoxy)-phenyl]-1H-pyrrolo[2,3-b]pyridin-5-yl}-benzamide;
2,4-Dichloro-N-{2-[3-(2-methoxy-ethoxy)-phenyl]-1H-pyrrolo[2,3-b]pyridin-5-yl}-benzamide;
2-Chloro-5-methoxy-N-{2-[3-(2-methoxy-ethoxy)-phenyl]-1H-pyrrolo[2,3-b]pyridin-5-yl}-benzamide; and
2-Chloro-N-{2-[3-(2-methoxy-ethoxy)-phenyl]-1H-pyrrolo[2,3-b]pyridin-5-yl}-benzamide.

Another embodiment of the invention are the compounds according to formula I, wherein
- $R^1$ is a phenyl group optionally substituted with —X-alkyl;
  - wherein the alkyl group is optionally substituted one or several times by halogen, hydroxy, alkoxy, amino, alkylamino or dialkylamino;
- X is —CH$_2$—S(O)$_2$NH—, —NHS(O)$_2$—, —S(O)$_2$NH—, —S(O)$_2$— or —S(O)—;
- $R^4$ is hydrogen; and
- A is =CH—.

Another embodiment of the invention are the compounds according to formula I, wherein
- $R^1$ is a phenyl group optionally substituted with —X-alkyl;
  - wherein the alkyl group is optionally substituted one or several times by halogen, hydroxy, alkoxy, amino, alkylamino or dialkylamino;
- X is —NRC(O)— or —C(O)NR—;
- $R^4$ is hydrogen; and
- A is =CH—.

Such a compound is for example:
N-[2-(3-Acetylamino-phenyl)-1H-pyrrolo[2,3-b]pyridin-5-yl]-4-methoxy-benzamide;
N-[2-(3-Acetylamino-phenyl)-1H-pyrrolo[2,3-b]pyridin-5-yl]-2-chloro-6-methyl-benzamide;
N-[2-(3-Acetylamino-phenyl)-1H-pyrrolo[2,3-b]pyridin-5-yl]-2-methoxy-benzamide;
N-[2-(3-Acetylamino-phenyl)-1H-pyrrolo[2,3-b]pyridin-5-yl]-2,4-dichloro-benzamide;
N-[2-(3-Acetylamino-phenyl)-1H-pyrrolo[2,3-b]pyridin-5-yl]-2-chloro-5-methoxy-benzamide; and
N-[2-(3-Acetylamino-phenyl)-1H-pyrrolo[2,3-b]pyridin-5-yl]-2-chloro-benzamide.

Another embodiment of the invention are the compounds according to formula I, wherein
- $R^1$ is a heteroaryl group optionally substituted with halogen, nitro, amino or —Z-alkyl;
  - wherein the alkyl group is optionally substituted one or several times by halogen, hydroxy, alkoxy, amino, alkylamino or dialkylamino;
- $R^4$ is hydrogen; and
- A is =CH—.

Another embodiment of the invention are the compounds according to formula I, wherein
- $R^1$ is a pyridyl, thienyl or benzimidazolyl group optionally substituted with halogen, nitro, amino, heterocyclyl or —Z-alkyl;
  - wherein the alkyl group is optionally substituted one or several times by halogen, hydroxy, alkoxy, amino, alkylamino or dialkylamino;
- $R^4$ is hydrogen; and
- A is =CH—.

Another embodiment of the invention are the compounds according to formula I, wherein
- $R^1$ is a pyridyl group optionally substituted with halogen, nitro, amino, —Z-alkyl;
  - wherein the alkyl group is optionally substituted one or several times by halogen, hydroxy, alkoxy, amino, alkylamino or dialkylamino;
- $R^4$ is hydrogen; and
- A is =CH—.

Another embodiment of the invention are the compounds according to formula I, wherein
- $R^1$ is a thienyl or benzimidazolyl group optionally substituted with —Z-alkyl;
- Z is a single bond;
- $R^4$ is hydrogen; and
- A is =CH—.

Another embodiment of the invention are the compounds according to formula I, wherein
- $R^1$ is a phenyl group optionally substituted one to three, preferably one or two times with halogen, nitro, amino, —C(O)OH, heterocyclyl, —S(O)$_2$NH$_2$ or —X-alkyl;
  - or a heteroaryl group optionally substituted one or two times with heterocyclyl or —Z-alkyl;
  - and all alkyl groups are optionally substituted one or two times by hydroxy, alkoxy or dialkylamino;
- X is —NR—, —O—, —S—, —S(O)$_2$—, —S(O)—, —NRC(O)— or —C(O)NR—;
- Z is a single bond or —NR—;

R is hydrogen or alkyl, wherein the alkyl is optionally substituted one or two times by alkoxy;

$R^2$ and $R^3$ independently represent hydrogen, halogen, nitro, amino, alkoxy or alkyl; and $R^4$ is hydrogen.

Such compounds, for example, may be selected from the group consisting of:

2-Chloro-N-{2-[3-(3-methoxy-propionylamino)-phenyl]-3H-imidazo[4,5-b]pyridin-6-yl}-benzamide;
2-Chloro-N-{2-[4-(4-methyl-piperazin-1-yl)-phenyl]-3H-imidazo[4,5-b]pyridin-6-yl}-benzamide;
2-Chloro-N-{2-[3-(2-hydroxy-ethyl)-phenyl]-3H-imidazo[4,5-b]pyridin-6-yl}-benzamide;
2-Chloro-N-(2-{3-[2-methoxy-1-methoxymethyl-ethylcarbamoyl]-phenyl}-3H-imidazo[4,5-b]pyridin-6-yl)-benzamide;
2-Chloro-N-[2-(6-morpholin-4-yl-pyridin-3-yl)-3H-imidazo[4,5-b]pyridin-6-yl]-benzamide;
2-Chloro-N-[2-(4-methanesulfonyl-phenyl)-3H-imidazo[4,5-b]pyridin-6-yl]-benzamide;
2-Methoxy-N-{2-[4-(2-methoxy-ethoxy)-phenyl]-1H-pyrrolo[2,3-b]pyridin-5-yl}-benzamide;
N-(2-{4-[Bis-(2-methoxy-ethyl)-amino]-3-fluoro-phenyl}-3H-imidazo[4,5-b]pyridin-6-yl)-2-chloro-benzamide; and
2-Chloro-N-{2-[2-(3-methoxy-propylamino)-pyridin-4-yl]-3H-imidazo[4,5-b]pyridin-6-yl}-benzamide.

Another embodiment of the invention are the compounds according to formula I, wherein $R^1$ is a phenyl group optionally substituted one to three, preferably one or two times with —X-alkyl; and the alkyl group is optionally substituted one or two times by alkoxy;

X is —O— or —NRC(O)—;

R is hydrogen;

$R^2$ and $R^3$ independently represent hydrogen, chlorine, alkoxy or alkyl;

$R^4$ is hydrogen; and

A is =CH—.

Such compounds, for example, may be selected from the group consisting of:

2-Chloro-N-(2-phenyl-1H-pyrrolo[2,3-b]pyridin-5-yl)-benzamide;
2-Chloro-N-{2-[3-(2-methoxy-ethoxy)-phenyl]-1H-pyrrolo[2,3-b]pyridin-5-yl}-benzamide;
2-Methoxy-N-(2-phenyl-1H-pyrrolo[2,3-b]pyridin-5-yl)-benzamide;
2,4-Dichloro-N-(2-phenyl-1H-pyrrolo[2,3-b]pyridin-5-yl)-benzamide;
2-Chloro-6-methyl-N-(2-phenyl-1H-pyrrolo[2,3-b]pyridin-5-yl)-benzamide;
N-[2-(3-Acetylamino-phenyl)-1H-pyrrolo[2,3-b]pyridin-5-yl]-4-methoxy-benzamide;
2-Methyl-N-(2-phenyl-1H-pyrrolo[2,3-b]pyridin-5-yl)-benzamide;
2-Chloro-5-methoxy-N-{2-[3-(2-methoxy-ethoxy)-phenyl]-1H-pyrrolo[2,3-b]pyridin-5-yl}-benzamide;
2,4-Dichloro-N-{2-[3-(2-methoxy-ethoxy)-phenyl]-1H-pyrrolo[2,3-b]pyridin-5-yl}-benzamide;
4-Methoxy-N-{2-[3-(2-methoxy-ethoxy)-phenyl]-1H-pyrrolo[2,3-b]pyridin-5-yl}-benzamide;
3,5-Dimethoxy-N-{2-[3-(2-methoxy-ethoxy)-phenyl]-1H-pyrrolo[2,3-b]pyridin-5-yl}-benzamide;
3,5-Dimethoxy-N-(2-phenyl-1H-pyrrolo[2,3-b]pyridin-5-yl)-benzamide;
N-{2-[3-(2-Methoxy-ethoxy)-phenyl]-1H-pyrrolo[2,3-b]pyridin-5-yl}-2-methyl-benzamide;
2-Methoxy-N-{2-[4-(2-methoxy-ethoxy)-phenyl]-1H-pyrrolo[2,3-b]pyridin-5-yl}-benzamide;
N-[2-(3-Acetylamino-phenyl)-1H-pyrrolo[2,3-b]pyridin-5-yl]-2-chloro-benzamide;
N-[2-(3-Acetylamino-phenyl)-1H-pyrrolo[2,3-b]pyridin-5-yl]-2,4-dichloro-benzamide;
N-[2-(3-Acetylamino-phenyl)-1H-pyrrolo[2,3-b]pyridin-5-yl]-2-methoxy-benzamide;
N-[2-(3-Acetylamino-phenyl)-1H-pyrrolo[2,3-b]pyridin-5-yl]-2-chloro-6-methyl-benzamide; and
N-[2-(3-Acetylamino-phenyl)-1H-pyrrolo[2,3-b]pyridin-5-yl]-2-chloro-5-methoxy-benzamide.

Another embodiment of the invention are the compounds according to formula I, wherein $R^1$ is a phenyl group optionally substituted one to three, preferably one or two times with fluorine, nitro, amino, —C(O)OH, heterocyclyl, —S(O)$_2$NH$_2$ or —X-alkyl; and the alkyl group is optionally substituted one or two times by hydroxy, alkoxy or dialkylamino;

X is —NR—, —O—, —S—, —S(O)$_2$—, —S(O)—, —NRC(O)— or —C(O)NR—;

R is hydrogen or alkyl, wherein the alkyl is optionally substituted one or two times by alkoxy;

$R^2$ and $R^3$ independently represent hydrogen, halogen, nitro, amino or alkyl;

$R^4$ is hydrogen; and

A is =N—.

Such compounds, for example, may be selected from the group consisting of:

2-Chloro-N-(2-phenyl-3H-imidazo[4,5-b]pyridin-6-yl)-benzamide;
2-Chloro-6-methyl-N-(2-phenyl-3H-imidazo[4,5-b]pyridin-6-yl)-benzamide;
2-Bromo-N-(2-phenyl-3H-imidazo[4,5-b]pyridin-6-yl)-benzamide;
2-Methyl-5-nitro-N-(2-phenyl-3H-imidazo[4,5-b]pyridin-6-yl)-benzamide;
2-Chloro-5-nitro-N-(2-phenyl-3H-imidazo[4,5-b]pyridin-6-yl)-benzamide;
N-(2-Phenyl-3H-imidazo[4,5-b]pyridin-6-yl)-benzamide;
2-Chloro-N-{2-[3-(3-methoxy-propionylamino)-phenyl]-3H-imidazo[4,5-b]pyridin-6-yl}-benzamide;
5-Amino-2-methyl-N-(2-phenyl-3H-imidazo[4,5-b]pyridin-6-yl)-benzamide;
5-Amino-2-chloro-N-(2-phenyl-3H-imidazo[4,5-b]pyridin-6-yl)-benzamide;
2-Chloro-N-{2-[4-(2-diethylamino-ethoxy)-phenyl]-3H-imidazo[4,5-b]pyridin-6-yl}-benzamide;
2-Chloro-N-{2-[4-(2-methoxy-ethoxy)-phenyl]-3H-imidazo[4,5-b]pyridin-6-yl}-benzamide;
2-Chloro-N-{2-[3-(2-methoxy-ethoxy)-phenyl]-3H-imidazo[4,5-b]pyridin-6-yl}-benzamide;
2-Chloro-N-[2-(3-nitro-phenyl)-3H-imidazo[4,5-b]pyridin-6-yl]-benzamide;
2-Chloro-N-[2-(4-morpholin-4-yl-phenyl)-3H-imidazo[4,5-b]pyridin-6-yl]-benzamide;
2-Chloro-N-{2-[4-(4-methyl-piperazin-1-yl)-phenyl]-3H-imidazo[4,5-b]pyridin-6-yl}-benzamide;
2-Chloro-N-{2-[3-(2-hydroxy-ethyl)-phenyl]-3H-imidazo[4,5-b]pyridin-6-yl}-benzamide;
3-[6-(2-Chloro-benzoylamino)-3H-imidazo[4,5-b]pyridin-2-yl]-benzoic acid;
3-(6-(2-chlorobenzoylamino)-3H-imidazo[4,5-b]pyridin-2-yl)-N-(3-methoxy-propyl)-benzamide;
3-(6-(2-chlorobenzoylamino)-3H-imidazo[4,5-b]pyridin-2-yl)-N-isopropyl-benzamide;

2-Chloro-N-(2-{3-[2-methoxy-1-methoxymethyl-ethylcarbamoyl]-phenyl}-3H-imidazo[4,5-b]pyridin-6-yl)-benzamide;

2-Chloro-N-[2-(3-methylsulfanyl-phenyl)-3H-imidazo[4,5-b]pyridin-6-yl]-benzamide;

2-Chloro-N-[2-(4-sulfamoyl-phenyl)-3H-imidazo[4,5-b]pyridin-6-yl]-benzamide;

2-Chloro-N-[2-(4-nitro-phenyl)-3H-imidazo[4,5-b]pyridin-6-yl]-benzamide;

2-Chloro-N-[2-(4-methylsulfanyl-phenyl)-3H-imidazo[4,5-b]pyridin-6-yl]-benzamide;

2-Chloro-N-[2-(3-methanesulfinyl-phenyl)-3H-imidazo[4,5-b]pyridin-6-yl]-benzamide;

2-Chloro-N-[2-(4-methanesulfonyl-phenyl)-3H-imidazo[4,5-b]pyridin-6-yl]-benzamide;

N-[2-(3-Amino-phenyl)-3H-imidazo[4,5-b]pyridin-6-yl]-2-chloro-benzamide;

N-[2-(3-Acetylamino-phenyl)-3H-imidazo[4,5-b]pyridin-6-yl]-2-chloro-benzamide; and N-(2-{4-[Bis-(2-methoxy-ethyl)-amino]-3-fluoro-phenyl}-3H-imidazo[4,5-b]pyridin-6-yl)-2-chloro-benzamide.

Another embodiment of the invention are the compounds according to formula I, wherein R$^1$ is a heteroaryl group optionally substituted one or two times with heterocyclyl or —Z-alkyl; and the alkyl group is optionally substituted one or two times by alkoxy;

Z is a single bond or —NR—;

R is hydrogen;

R$^2$ and R$^3$ independently represent hydrogen or halogen;

R$^4$ is hydrogen; and

A is =N—.

Such compounds, for example, may be selected from the group consisting of:

2-Chloro-N-(2-thiophen-2-yl-3H-imidazo[4,5-b]pyridin-6-yl)-benzamide;

2-Chloro-N-(2-thiophen-3-yl-3H-imidazo[4,5-b]pyridin-6-yl)-benzamide;

2-Chloro-N-[2-(2-methyl-pyridin-4-yl)-3H-imidazo[4,5-b]pyridin-6-yl]-benzamide;

2-Chloro-N-[2-(6-methyl-pyridin-3-yl)-3H-imidazo[4,5-b]pyridin-6-yl]-benzamide;

N-[2-(1H-Benzoimidazol-5-yl)-3H-imidazo[4,5-b]pyridin-6-yl]-2-chloro-benzamide;

2-Chloro-N-[2-(6-morpholin-4-yl-pyridin-3-yl)-3H-imidazo[4,5-b]pyridin-6-yl]-benzamide; and 2-Chloro-N-{2-[2-(3-methoxy-propylamino)-pyridin-4-yl]-3H-imidazo[4,5-b]pyridin-6-yl}-benzamide.

Still another embodiment of the invention is a process for the manufacture of the compounds of formula I, wherein (a) the compound of formula II

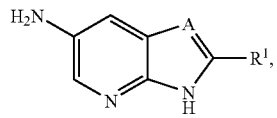

formula II wherein A and R$^1$ have the significance as given in formula I above, is reacted with a compound of formula III

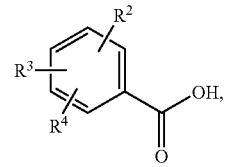

formula III wherein R$^2$, R$^3$ and R$^4$ have the significance given above for formula I, and wherein the carboxylic acid group is activated before the reaction, to give the respective compound of formula I, (c) said compound of formula I is isolated from the reaction mixture, and (d) if desired, converted into a pharmaceutically acceptable salt.

The derivatives of the general formula I or a pharmaceutically acceptable salt thereof, may be prepared by any process known to be applicable for the preparation of chemically-related compounds by the one skilled in the art. Such processes, when used to prepare the derivatives of formula I, or a pharmaceutically-acceptable salt thereof, are provided as a further feature of the invention and are illustrated by the following representative examples of scheme 1 and 2, in which, unless otherwise stated R$^1$, R$^2$, R$^3$, R$^4$ and A have the significance given herein before for formula I. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

Scheme 1

The manufacture of the compounds of formula I varies according to the nature of "A" in formula I. The compounds of the present invention wherein "A" is =N— can be prepared according to scheme 1, and are named I-A.

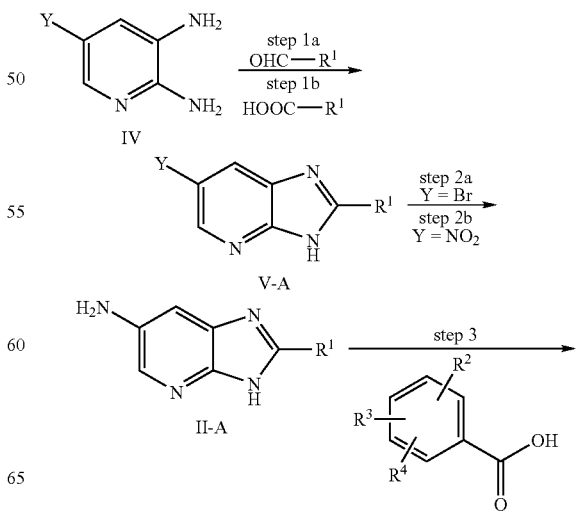

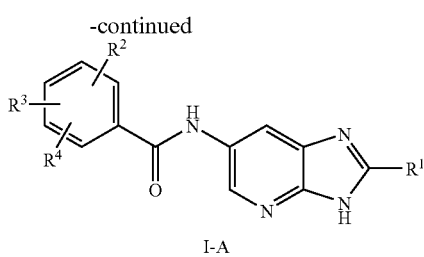

In scheme 1, $R^1$, $R^2$, $R^3$ and $R^4$ have the significance as given above for formula I and Y is bromine (for the route via step 2a) or nitro (for the route via step 2b).

Step 1a: Condensation of an aromatic aldehyde with a 2,3-diamino-pyridine derivative of formula IV can carried out at elevated temperatures from 60 to 200° C. in a suitable solvent like acetonitrile, nitrobenzene, N,N-dimethylformamide (DMF), dimethylsulfoxide (DMSO), xylene, or methoxyethanol, optionally in the presence of an oxidizing agent like oxygen or an iron (III) salt or sulfur, or 2,3-dichloro-5,6-dicyano-p-benzoquinone (DDQ).

Step 1b: The condensation with an aromatic carboxylic acid, or a suitable derivative thereof, with a 2,3-diamino-pyridine derivative of formula IV can be achieved at temperatures in the range of 100-220° C. with a condensation reagent like polyphosphoric acid, $POCl_3$, or $P_4O_{10}$, optionally in mixture with methane sulfonic acid.

Step 2a: In the compounds of formula V-A, wherein Y is bromine, such bromine can be replaced by an amino group by heating in aqueous ammonia in the presence of a catalyst like $CUSO_4$ or CuI. A solubilizing co-solvent like N-methylpyrrolidone (NMP) or dimethyl acetamide can be added, and the reaction is carried out at temperatures of 100-180° C. in a closed vessel.

Alternatively, the amino functionality may be introduced in protected form as a tert.-butoxycarbonylamino substituent via coupling under standard Hartwig/Buchwald conditions (for example, with a base like sodium tert. butoxide and a palladium catalyst like $Pd_2(dba)_3$ and a phosphine ligand like tri-tert. butyl phosphane).

Step 2b: For the compounds of formula V-A, wherein Y is nitro, the reduction of the nitro group is accomplished by standard conditions such as heterogeneous hydrogenation with Pd on charcoal as the catalyst, in solvents like methanol, ethanol, tetrahydrofuran (THF), or ethyl acetate, at room temperature or up to 80° C.; or by homogeneous hydrogenation with a Pd catalyst and triethyl ammonium formate in a solvent like methanol at reflux conditions. The reduction can also be carried out with base metals like iron or tin in acidic media like acetic acid or aqueous HCl, from room temperature to 120° C. Another suitable reductant would be ammonium sulfide in water or methanol, or tin (II) chloride in N,N-dimethylformamide dimethylformamide (DMF).

Step 3: Acylation of the amino moiety on the compounds of formula II-A can be done with an appropriate carboxylic acid of formula III in a two step procedure. In the first step, the carboxylic acid of the formula III becomes activated. This reaction is carried out in an inert solvent or diluent, for example, in dichloromethane, dioxane, tetrahydrofuran (THF) or N,N-dimethylformamide (DMF) in the presence of an activating agent. Suitable activating agents are, for example, oxalyl or thionyl chloride, isobutyl chloroformate, N-hydroxybenzotriazole, N,N'-carbonyldiimidazole, dicyclohexylcarbodiimide, N-(3-dimethylaminopropyl)-N'-ethylcarbodiimide (EDC), 2-morpholino-ethyl-isocyanide (MEI) and the like. Other activating agents can also be used and are well known to the skilled artist. The activated carboxylic acid derivative (e.g. the acid chloride) can be sometimes isolated as intermediate. Nevertheless the reaction is often carried out in a one-pot procedure without isolation of the activated carboxylic acid intermediate. In the second step, the amine of formula II-A is reacted with the activated carboxylic acid yielding the compounds of formula I-A. This reaction can be catalyzed sometimes by N,N-dimethylaminopyridine (DMAP) and the like If an excess of carboxylic acids of formula III is used, simultaneous acylation on the heterocyclic core can occur, e.g. on N-1 or N-3. Such a bis-acylated intermediate can be cleaved easily to the desired mono-acylated compound by subsequent treatment with ammonia in water or methanol at room temperature.

Scheme 2

The manufacture of the compounds of formula I varies according to the nature of "A" in formula I. The compounds of the present invention wherein "A" is =C— can be prepared according to scheme 2, and are named I-B.

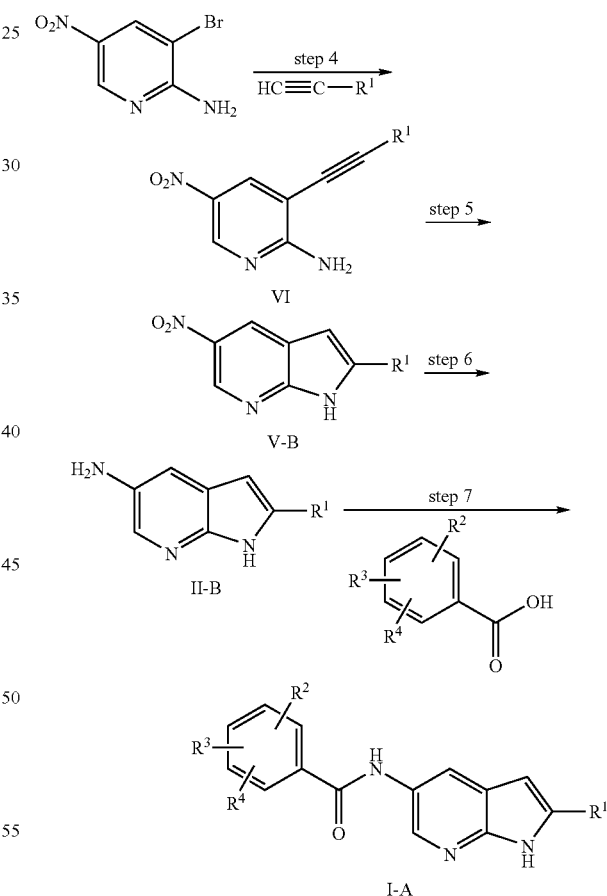

In scheme 1, $R^1$, $R^2$, $R^3$ and $R^4$ have the significance as given above for formula I.

Step 4: An ethynyl-arene can be coupled with 3-bromo-5-nitro-pyridin-2-ylamine under standard conditions of the so called Sonogashira reaction, with a copper catalyst like CuI or CuCl, and a palladium catalyst like $PdCl_2(PPh_3)_2$ or $PdCl_2(PhCN)_2$/$PtBu_3$, and a base like triethyl amine or di-isopropyl amine, in an inert solvent like tetrahydrofuran (THF), dioxane, N,N-dimethylformamide (DMF), or acetonitrile. The reaction proceeds at room temperature or higher, up to 160° C.

Alternatively, the ethynyl-arene may first be converted into a more reactive alkynyl-Zn or —Sn derivative by procedures known in the art: the ethynyl-arene is deprotonated with a strong base like butyl lithium to form an alkynyl-Li intermediate which is reacted with $ZnCl_2$ or $Bu_3SnCl$ to yield the desired zinc or tin intermediate. These may subsequently be coupled to the bromopyridine under standard cross coupling conditions, for instance by catalysis by a palladium phosphine complex like $Pd(PPh_3)_4$ or $PdCl_2(PPh_3)_2$ or $Pd_2(dba)_3$/$PtBu_3$ in solvents like dimethyl acetamide, tetrahydrofuran (THF), or toluene.

Step 5: Cyclisation of the alkyne intermediate to form a pyrrole ring can be achieved by treatment with a base like potassium tert. butoxide, potassium hydride, or sodium ethoxide in an inert solvent like N-methylpyrrolidone (NMP), tetrahydrofuran (THF), or N,N-dimethylformamide (DMF), or ethanol, at temperatures in the range from room temperature to reflux. Alternatively, the base can be replaced by a catalyst like CuI.

Step 6 and Step 7: These step are analogous to Step 2b and Step 3 under scheme 1 above.

Certain substituents on the group $R^1$, $R^2$, $R^3$ and $R^4$ may not be inert to the conditions of the synthesis sequences described above and may require protection by standard protecting groups known in the art. For instance, an amino or hydroxyl group maybe protected as a tert.-butoxycarbonyl derivative. Alternatively, some substituents may be derived from others at the end of the reaction sequence. For instance, a compound of formula I may be synthesized bearing a nitro- or an ethoxycarbonyl or an alkylsulfanyl substituent on the group $R^1$, which substituents are finally converted to an amino-, acylamino-, or alkylsulfonylamino substituent, or to a carboxamide substituent, or to an alkylsulfinyl or alkylsulfonyl substituent by standard procedures.

The compounds of the general formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid. Alternatively separation of the enantiomers can also be achieved by using chromatography on chiral HPLC-phases which are commercially available.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethylammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Stahl, P. H., and Wermuth, G., (editors), Handbook of Pharmaceutical Salts, Verlag Helvetica Chimica Acta (VHCA), Zürich (2002) or Bastin, R. J., et al., Organic Proc. Res. Dev. 4 (2000) 427-435.

The compounds according to this invention and their pharmaceutically acceptable salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

An embodiment of the invention is a medicament containing one or more compounds according to formula I as active ingredients together with pharmaceutically acceptable adjuvants.

Another embodiment of the invention is said medicament for the treatment of diseases mediated by an inappropriate activation of src family tyrosine kinases.

Another embodiment of the invention is said medicament for the treatment of inflammatory-, immunological-, CNS disorders or bone diseases.

Another embodiment of the invention is said medicament for the treatment of cancer.

Another embodiment of the invention is the use of one or more compounds according to formula I for the manufacture of medicaments for the treatment of diseases mediated by an inappropriate activation of src family tyrosine kinases.

Another embodiment of the invention is the use of one or more compounds according to formula I for the manufacture of medicaments for the treatment of cancer.

Another embodiment of the invention is the use of one or more compounds according to formula I for the manufacture of medicaments for the treatment of inflammatory-, immunological-, CNS disorders or bone diseases.

Another embodiment of the invention is the use of one or more compounds according to formula I as src family tyrosine kinase inhibitors.

Another embodiment of the invention is the use of one or more compounds according to formula I as cell signaling-regulating and anti-proliferating agents.

Another embodiment of the invention is the use of one or more compounds according to formula I for the treatment of inflammatory-, immunological-, CNS disorders or bone diseases.

Another embodiment of the invention is the use of one or more compounds of formula I according to formula I for the treatment of cancer.

A pharmaceutical preparation was obtained e.g. by using the following procedure:
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads:gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 μm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenise.

The above described preparation yields micro-suspensions of the compounds of formula I with particle sizes between 1 and 10 μm. The suspensions are suitable for oral applications and were used in the in vivo pharmacokinetic testings described below.

Pharmacological Activity:

The activity of the compounds according to this invention as inhibitors for the src-family tyrosine kinases was shown by using the following assay.

SRC-Inhibitor-Assay Parameters:

| SRC-Inhibitor-Assay Parameters: | | |
| --- | --- | --- |
| Reaction mixture: | | |
| ATP | | 5 μM |
| Peptide (Ro + Ja133-Ro): | | 10 μM |
| Ja133-Ro: | | 196 nM |
| Ro: | | 9.8 μM |
| PT66 | | 230 ng/ml |
| Assay buffer: | | 4 mM MgCl2 |
| | | 2 mM TCEP |
| | | 50 mM HEPES |
| | | 0, 1% Tween 20 |
| | | pH 7.3 |
| Enzyme: | | 2.5 U/ml |
| Inhibitor: | | max. 25 μM |
| | | min. 0.42 nM |
| Material: | | |
| Eu-labelled phosphotyrosine antibody: | | for Lck Cisbio Mab PT66-K, for Src EG&G Wallac PT66 Eu-W1024 (all commercially available). |
| Peptides: | Ro: | NH2-A-E-E-E-I-Y-G-E-F-E-A-K-K-K-K-CONH$_2$, and |
| | Ja133-Ro: | Ja133-G-Aminocaprylic acid-A-E-E-E-I-Y-G-E-F-E-A-K-K-K-K-CONH$_2$, wherein Ja133 is LightCycler-Red 640-N-hydroxy succinimide ester; whereby both peptides were synthesized by an optimized solid phase peptide synthesis protocol (Merrifield, Fed. Proc. Fed. Amer. Soc. Exp. Biol. 21 (1962) 412) on a Zinsser SMP350 peptide synthesizer. Shortly, the peptide was assembled on 160 mg (22.8 μmol scale) of a Rink-Linker modified polystyrene solid phase by repeatedly conjugating an twenty fold excess of amino acids each protected by temporary piperidine labile Fmoc— and permanent acid labile tert-Bu—, BOC— and O-tert-Bu-groups depending on the side chain function. The substrate sequence AEEEIYGEFEAKKKK was N-terminal additionally mounted with the spacer amino acids Aminocaprylic acid and Glycin. After cleavage of the N-terminal temporary protecting group the still attached and protected peptide was labeled with a 1.5 fold amount of LightCycler-Red 640-N-hydroxy succinimide ester (purchased from Roche Diagnostics GmbH) and triethylamine. After 3 hrs. the resin was washed with Dimethylformamide and Isopropanol until the eluates of the blue resin got colourless. The fully protected and labeled peptide was removed from the solid phase and released from the permanent protecting groups by treatment with a mixture of 80% trifluoroacetic acid, 10% Ethanedithiol, 5% Thioanisol and 5% Water. The substrate was finally isolated by a preparative reverse phase HPLC purification. The purification yielded 12.2 mg RP-HPLC single peak pure blue material (lyophilisate). The identity was proven by MALDI mass spectroscopy [2720.0]. |
| Enzymes: | | Upstate Lck (p56$^{lck}$, active), Upstate Src (p60$^{c-src}$, partially purified) were purchased from UBI, Upstate Biotech, Inc. |

Time-resolved Fluorescence Assay: Reader: Perkin Elmer, Wallac Viktor 1420-040 multilabel counter; Liquid handling system: Beckman Coulter, Biomek 2000.

ATP, Tween™ 20, 4-(2-hydroxyethyl)-1-piperazineethanesulfonic acid (HEPES) were purchased from Roche Molecular Biochemicals, $MgCl_2$ and $MnCl_2$ were purchased from Merck Eurolab, Tris(2-carboxyethyl)phosphine hydrochloride (TCEP) was purchased from Pierce, 384 Well low volume fluorescence plates was purchased from Falcon.

Assay Description:

At first the enzyme is pre-incubated for 15 min. at 15° C. in aqueous solution with corresponding amounts of inhibitors according to this invention. Then the phosphorylation reaction is started by adding a reaction mixture, containing ATP, Peptide and PT66, and subsequent shaking. The proceeding of this reaction is immediately monitored using time resolved fluorescence spectroscopy in a suitable well plate reader.

The $IC_{50}$-values can be obtained from the reaction rates by using a non-linear curve fit (XLfit software (ID Business Solution Ltd., Guilford, Surrey, UK))

| Example-No. | IC50 src [µM] | IC50 lck [µM] |
| --- | --- | --- |
| 4-5 | 0.007 | 0.049 |
| 1-1 | 0.021 | 0.481 |
| 2-1 | 0.135 | 0.160 |
| 1-2, 1-3, 1-6, 1-7, 3-1, 4-1, 4-2, 4-6, 4-7, 4-8, 6-3, 7-2, 7-3, 7-5, 7-7, 9-1, 10-1, 11-1, 12-1, 12-12, 12-4, 12-5, 12-7, 12-14, 13-1, 14-1 | 0.005-0.300 | 0.040-9.000 |
| 1-4, 1-5, | 0.300-3.500 | 1.000-9.000 |

The following examples and references are provided to aid the understanding of the present invention, the true scope of which is set forth in the appended claims. It is understood that modifications can be made in the procedures set forth without departing from the spirit of the invention.

EXAMPLES

Starting Materials 5-bromo-2,3-diaminopyridine was purchased from Aldrich.

2,3-diamino-5-nitropyridine was prepared as described in Cai, S. X., et al, J. Med. Chem. 40 (1997) 3679-3686.

The substituted benzaldehydes used are known in the art and prepared by literature procedures, for instances as described for 4-morpholino-benzaldehyde in Magdolen, P., et al, Tetrahedron 5 (2001) 4781-4785, or as described below:

4-(2-Diethylamino-ethoxy)-benzaldehyde 4.82 g potassium hydroxide were dissolved in 70 ml ethanol and treated with 8.46 g (2-Chloro-ethyl)-diethyl-amine hydrochloride. The mixture was stirred until everything was dissolved, then 5.0 g benzaldehyde were added and refluxed for 16 hrs. The mixture was diluted with water and extracted with ethyl acetate, and the organic phases washed several times with caustic soda. After drying and evaporation of the solvent the crude product was used without further purification. Yield 3.90 g 3-[2-(Tetrahydro-pyran-2-yloxy)-ethyl]-benzaldehyde 2.14 g (7.52 mmol) 2-[2-(3-Bromo-phenyl)-ethoxy]-tetrahydro-pyran in 9 ml dry THF were cooled to −78 C and treated dropwise with 9.87 ml of 1.6M solution of butyl lithium in hexane (15.79 mmol). After stirring for 30 min, 2.31 g (31.58 mmol) N,N-dimethylformamide were added dropwise and stirring was continued for another 15 min at −78 C. The mixture was slowly warmed to room temperature and stirred for and another 60 min. Water and dichloromethane were added, the organic phase separated, and the aqueous phase extracted several times with dichloromethane. The combined organic phases were dried, evaporated and the residue purified by chromatography on silica in ethyl acetate heptane mixtures. Yield 1.66 g of the title compound as a pale yellow oil.

N-(3-Formyl-phenyl)-3-methoxy-propionamide 0.76 g (7.31 mmol) 3-methoxypropionic acid in 10 ml dry N,N-dimethylformamide (DMF) were treated with 1.25 g (7.71 mmol) 1,1'-carbonyl-diimidazole and stirred for 1 hr at room temperature. 1.00 g 3-aminobenzylalcohol were added and stirring was continued over night. The solvent was removed and the residue chromatographed on silica in ethyl acetate, yielding 1.26 g N-(3-Hydroxymethyl-phenyl)-3-methoxy-propionamide.

The above 1.26 g N-(3-Hydroxymethyl-phenyl)-3-methoxy-propionamide were dissolved in 50 ml acetone, 12.60 g manganese dioxide were added and the mixture stirred at room temperature over night. The mixture was filtered and the filtrate evaporated and further purified by chromatography on silica in ethyl acetate/heptane mixtures. Yield 0.77 g of the title compound as a colourless oil.

Substituted phenyl-acetylenes were prepared by acylation of 3- or 4-amino-phenylacetylene by literature procedures, as described in U.S. Pat. No. 4,162,265A, or by alkylation of 3- or 4-hydroxyphenylacetylene by literature procedures. For instance, 3-(2-methoxyethoxy)phenylacetylene 3-Hydroxyphenylacetylene (237 mg, 2 mmol) was heated with 2-bromoethylmethylether (0.23 mL, 2.4 mmol) and potassium carbonate (322 mg, 2.4 mmol) in acetone (5 mL) to 110° C. in a microwave oven (CEM Discover) for 45 minutes. Water (1 mL) was added to the mixture and the whole was extracted with dichloromethane (2×25 mL). The combined organics were dried over $MgSO_4$, filtered and concentrated in vacuo to afford a brown oil. The oil was purified by column chromatography ($SiO_2$, dichloromethane) to afford 3-(2-methoxyethoxy)phenylacetylene as a colourless oil (247 mg, 70% yield).

¹H-NMR (400 MHz; CDCl₃): δ=7.23 (1H, dd, J 8.8, 8.0), 7.08 (1H, dt, J 7.6, 1.2), 7.04 (1H, dd, J 1.48, 2.7), 6.94 (1H, ddd, J 1.0, 2.6, 8.3), 4.11 (2H, t, J 4.6), 3.74 (2H, t, J 4.6), 3.45 (3H, s), 3.05 (1H, s).

Alternatively, 4-(2-methoxyethoxy)phenylacetylene was prepared from the corresponding iodobenzene and trimethylsilylacetylene by Sonogashira coupling, as described for 4-methoxyphenylacetylene in Tsuji, M., J. Org. Chem. 68 (2003) 9589-9597-supporting information S. 1-36-http://pubs.acs.org/subscribe/journals/joceah/suppinfo/jo035090f/jo035090fsi20030 918 025110.pdf.

3-(acetylamino)phenylacetylene

Acetic anhydride (13.8 mL, 144 mmol) was added dropwise to a solution of 3-ethynylaniline (14.0 g, 120 mmol) and 4-(Dimethylamino-)pyridine (DMAP) (1.5 g, 12 mmol) in tetrahydrofuran (300 mL). The mixture was stirred at room temperature for 2 hours, water (100 mL) was added to the mixture and the whole was extracted with dichloromethane (2×250 mL). The combined organics was washed with 10% citric acid (100 mL) followed by saturated sodium bicarbonate solution (100 mL), dried over MgSO₄, filtered and concentrated in vacuo to afford 3-(acetylamino)phenylacetylene as a yellow solid (18.3 g, 96%).

¹H-NMR (400 MHz; CDCl₃): δ=7.62 (1H, s), 7.53 (1H, d, J 7.7), 7.41 (1H, br.s), 7.28-7.22 (2H, m), 3.06 (1H, s), 2.17 (3H, s).

6-Morpholin-4-yl-nicotinic acid 3.00 g 6-chloronicotinic acid in 24 ml dry acetonitrile were mixed with 16.6 ml morpholine and heated to reflux for 48 hrs. The mixture was evaporated under vacuum and the residue dissolved in water. The crude product was precipitated by addition of 10% aqueous acetic acid, isolated by filtration and washed with water and methanol to give 1.83 g of the title compound.

Final Products

Example 1-1

2-Chloro-N-(2-phenyl-3H-imidazo[4,5-b]pyridin-6-yl)-benzamide a) 6-Nitro-2-phenyl-3H-imidazo[4,5-b]pyridine 14.05 g 2,3-diamino-5-nitropyridine and 9.68 g benzaldehyde in 250 ml nitrobenzene were heated to 140-150° C. for 15 hrs. The solvent is removed by vacuum distillation and the residue is dispersed in ethyl acetate, filtered, and the filter residue washed thoroughly with ethyl acetate.
Yield 16.0 g b) 2-phenyl-3H-imidazo[4,5-b]pyridin-6-ylamine 12.0 g 6-nitro-2-phenyl-3H-imidazo[4,5-b]pyridine were dissolved in 1 l acetic acid. 18 g iron powder were added and the mixture heated to 80° C. with stirring. After 2 hrs the mixture was cooled to room temperature and filtered over Celite. The celite pad was washed with methanol and the combined filtrates were evaporated. The residue was dissolved methanol/dichloromethane 1:1 and filtered over silica. The filtrate was concentrated to a volume of 100 ml, the resulting precipitate collected by filtration and washed with methanol. Yield 7.68 g 2-Chloro-N-(2-phenyl-3H-imidazo[4,5-b]pyridin-6-yl)-benzamide 100 mg 2-phenyl-3H-imidazo[4,5-b]pyridin-6-ylamine (0.38 mmol,) in 4 ml dry pyridine were cooled to –40° C. and treated with 92 mg (1.1 equivalents) 2-chlorobenzoyl chloride. The cooling bath was removed an the mixture stirred for 1 hr at room temperature. The solvent was evaporated and the residue purified by chromatography on silica in methanol/dichloromethane mixtures. Yield 35 mg.

¹H-NMR (400 MHz, CD₃OD): δ=8.66 (broad s) and 8.53 (broad s, together 2H); 8.18 (m, 2H); 7.65-7.48 (m, 7H).

The following examples were obtained in analogous fashion as described for example 1-1:

| Example-No. | Systematic Name | ¹H-NMR |
|---|---|---|
| 1-2 | 2-Chloro-6-methyl-N-(2-phenyl-3H-imidazo[4,5-b]pyridin-6-yl)-benzamide | |
| 1-3 | 2-Bromo-N-(2-phenyl-3H-imidazo[4,5-b]pyridin-6-yl)-benzamide | (400 MHz, d⁶-DMSO): δ = 13.45 (s) and 13.08 (s, together 1H); 10.79 (broad s) and 10.68 (broad s, together 1H); 8.56 (s) and 8.45 (s, together 2H); 8.20 (m, 2H); 7.77-7.46 (m, 7H). |
| 1-4 | 2-Methyl-5-nitro-N-(2-phenyl-3H-imidazo[4,5-b]pyridin-6-yl)-benzamide | (400 MHz, d⁶-DMSO): δ = 10.81 (broad s, 1H); 8.59 (s) and 8.51 (broad s) and 8.41 (s, together 3H); 8.34-8.13 (m, 4H); 7.67-7.54 (m, 5H); 2.56 (s, 3H). |
| 1-5 | 2-Chloro-5-nitro-N-(2-phenyl-3H-imidazo[4,5-b]pyridin-6-yl)-benzamide | (400 MHz, d⁶-DMSO): δ = 13.63 (s) and 13.13 (s, together 1H); 11.05 (s) and 10.92 (s, together 1H); 8.54 (m) and 8.44 (s, together 3H); 8.37 (d, 1H); 8.25 (d, 1H); 8.20 (d, 1H); 7.93 (d, 1H); 7.66 (m, 3H). |
| 1-6 | N-(2-Phenyl-3H-imidazo[4,5-b]pyridin-6-yl)-benzamide | (400 MHz, CD₃OD): δ = 8.62 (broad s, 2H) 8.18 (m, 2H); 8.01 (m, 2H); 7.62-7.55 (m, 6H). |

-continued

| Example-No. | Systematic Name | ¹H-NMR |
|---|---|---|
| 1-7 | 2-Chloro-N-{2-[3-(3-methoxy-propionylamino)-phenyl]-3H-imidazo[4,5-b]pyridin-6-yl}-benzamide | (400 MHz, d⁶-DMSO): δ = 13.03 (broad s, 1H); 10.79 (broad s, 1H); 10.18 (s, 1H); 8.56 (d) and 8.54 (broad s, together 3H); 7.66 (d, 1H); 7.60 (d, 1H); 7.55 (d, 1H); 7.53 (d, 1H); 7.52-7.49 (m, 3H); 3.66 (t, 2H); 3.27 (s, 3H); 2.61 (t, 2H). |

Example 2-1

5-Amino-2-methyl-N-(2-phenyl-3H-imidazo[4,5-b]pyridin-6-yl)-benzamide 1.80 g of the product from example 1-4 were dissolved in 30 ml methanol and 30 ml tetrahydrofuran (THF) and hydrogenated with 0.5 g 10% palladium on charcoal at room temperature for 45 min. The catalyst was removed by filtration over a small pad of silica and the silica was washed thoroughly with methanol/THF 1:1. Evaporation of the filtrates gave 1.11 g of the title product.

¹H-NMR (400 MHz, d⁶-DMSO): δ=13.50 (s) and 13.08 (s, together 1H); 10.43 (s, 1H); 8.61 (s, 1H); 8.51 (broad s, 1H); 8.21 (d, 2H); 7.61-7.52 (m, 3H); 6.96 (d, 1H); 6.74 (s, 1H); 6.60 (d, 1H); 5.18 (broad s, 2H); 2.24 (s, 3H).

Example 3-1

5-Amino-2-chloro-N-(2-phenyl-3H-imidazo[4,5-b]pyridin-6-yl)-benzamide 700 mg of the product from example 1-5 in 30 ml ethanol were cooled in a water bath at room temperature. 1.20 g tin (II) chloride and 2 ml conc. HCl were slowly added and the mixture was stirred for 1 hr at 40° C. The solvent was evaporated and the residue adjusted to pH 5 with aqueous sodium carbonate solution. After dilution with water the precipitate was isolated by filtration and washed with water and ether. The filter residue was dispersed in methanol and filtered again over a pad of Celite. The Celite pad was washed thoroughly with methanol, and the combined filtrates were evaporated. The residue was purified by preparative HPLC. Yield 192 mg.

¹H-NMR (400 MHz, d⁶-DMSO): δ=13.20 (broad s, 1H); 10.63 (s, 1H); 8.58 (s, 1H); 8.49 (s, 1H); 8.21 (d, 2H); 7.61-7.52 (m, 3H); 7.17 (d, 1H); 6.77 (s, 1H); 6.68 (d, 1H); 5.50 (broad s, 2H).

Example 4-1

2-Chloro-N-{2-[4-(2-diethylamino-ethoxy)-phenyl]-3H-imidazo[4,5-b]pyridin-6-yl}-benzamide a) {2-[4-(6-Bromo-3H-imidazo[4,5-b]pyridin-2-yl)-phenoxy]-ethyl}-diethyl-amine 3.31 g 5-bromo-2,3-diaminopyridine and 3.90 g 4-(2-diethylaminoethoxy)-benzaldehyde in 120 ml nitrobenzene were heated to 140-150° C. for 24 hrs. The solvent was removed by vacuum distillation. The residue was dispersed in ethyl acetate and the crude product was isolated by filtration and washed thoroughly with more ethyl acetate. Yield 1.45 g b) 2-[4-(2-Diethylamino-ethoxy)-phenyl]-3H-imidazo[4,5-b]pyridin-6-ylamine To 250 mg of the product from example 4-1a) in 1 ml N-Methylpyrrolidone (NMP) were added 32 mg copper sulfate pentahydrate and 3.1 ml conc. ammonia. The mixture was heated in a cap glass vial in a microwave oven at 151° C. and 18 bar for 5 hrs. After cooling, the mixture was diluted with methanol, filtered, and evaporated. The residue was transferred in water onto a short column of RR (C-18) silica and eluted with water. Evaporation of the eluent gave 105 mg of the title product.

2-Chloro-N-{2-[4-(2-diethylamino-ethoxy)-phenyl]-3H-imidazo[4,5-b]pyridin-6-yl}-benzamide 100 mg of the product from example 4-1b) in 4 ml dry pyridine were treated at room temperature with 161 mg 2-chlorobenzoyl chloride. The mixture was stirred for 16 hrs and evaporated. The residue was dissolved in 3 ml methanol and stirred with 1 ml conc. ammonia for 1 hr. The solvents were removed under vacuum and the residue purified by preparative HPLC. Yield 46 mg.

¹H-NMR (500 MHz, d⁶-DMSO): δ=10.56 (s, 1H); 8.45 (s, 1H); 8.33 (s, 1H); 8.15 (d, 2H); 7.64 (m, 1H); 7.59 (d, 1H); 7.53 (m, 1H); 7.48 (m, 1H); 7.09 (d, 2H); 4.11 (t, 2H); 2.82 (t, 2H); 2.58 (q, not separated from DMSO); 1.00 (t, 6H).

The following examples were obtained in analogous fashion as described for example 4-1:

| Example-No. | Systematic Name | ¹H-NMR |
|---|---|---|
| 4-2 | 2-Chloro-N-{2-[4-(2-methoxy-ethoxy)-phenyl]-3H-imidazo[4,5-b]pyridin-6-yl}-benzamide | (400 MHz, CD₃OD): δ = 8.62 (broad s) and 8.49 (broad s, together 2H); 8.12 (d, 2H); 7.65 (d, 1H); 7.58-7.47 (m, 3H); 7.16 (d, 2H); 4.25 (t, 2H); 3.81 (t, 2H); 3.47 (s, 3H). |

-continued

| Example-No. | Systematic Name | $^1$H-NMR |
|---|---|---|
| 4-3 | 2-Chloro-N-{2-[3-(2-methoxy-ethoxy)-phenyl]-3H-imidazo[4,5-b]pyridin-6-yl}-benzamide | (400 MHz, d$^6$-DMSO): δ = 13.52 (s) and 13.05 (s, together 1H); 10.82 (s) and 10.70 (s, together 1H); 8.60 (s) and 8.55 (s) and 8.45 (s, together 2H); 7.82 (broad s) and 7.77 (broad s, together 2H); 7.70-7.45 (m, 5H); 7.12 (broad s, 1H); 4.22 (broad s, 2H); 3.73 (broad s, 2H). |
| 4-4 | 2-Chloro-N-[2-(3-nitro-phenyl)-3H-imidazo[4,5-b]pyridin-6-yl]-benzamide | (400 MHz, d$^6$-DMSO): δ = 10.82 (s, 1H); 8.97 (s, 1H); 8.57 (d) and 8.52 (s) and 8.45 (s, together 3H); 8.28 (d, 1H); 7.80 (t, 1H); 7.65-7.58 (m, 4H). |
| 4-5 | 2-Chloro-N-[2-(4-morpholin-4-yl-phenyl)-3H-imidazo[4,5-b]pyridin-6-yl]-benzamide | (400 MHz, d$^6$-DMSO): δ = 13.25 (s) and 12.80 (s, together 1H), 10.74 (s) and 10.63 (s, together 1H); 8.49-8.34 (m, 2H); 8.07 (d, 2H); 7.65-7.54 (m, 4H); 7.11 (s, 2H); 3.76 (s, 4H); 3.27 (s, not separated from H2O). |
| 4-6 | 2-Chloro-N-(2-thiophen-2-yl-3H-imidazo[4,5-b]pyridin-6-yl)-benzamide | (400 MHz, d$^6$-DMSO): δ = 13.60 (s) and 13.12 (s, together 1H), 10.80 (s) and 10.68 (s, together 1H); 8.57-8.37 (dd, 2H); 7.93 (d) and 7.81 (s, together 2H); 7.67-7.49 (m, 4H); 7.27 (s, 1H). |
| 4-7 | 2-Chloro-N-(2-thiophen-3-yl-3H-imidazo[4,5-b]pyridin-6-yl)-benzamide | (400 MHz, d$^6$-DMSO): δ = 13.43 (s) and 12.99 (s, together 1H), 10.79 (s) and 10.68 (s, together 1H); 8.56-8.51 (t) and 8.40-8.30 (t, together 3H); 7.83-7.76 (m, 2H); 7.67-7.49 (m, 4H). |
| 4-8 | 2-Chloro-N-{2-[4-(4-methyl-piperazin-1-yl)-phenyl]-3H-imidazo[4,5-b]pyridin-6-yl}-benzamide | (400 MHz, CD$_3$OD): δ = 8.57 (s, 1H); 8.47 (s, 1H); 8.06 (d, 2H); 7.64 (d, 1H); 7.58-7.47 (m, 3H); 7.15 (d, 2H); 3.47 (s, 4H); 2.86 (s, 4H); 2.54 (s, 3H). |

Example 4-9

2-Chloro-N-{2-[3-(2-hydroxy-ethyl)-phenyl]-3H-imidazo[4,5-b]pyridin-6-yl}-benzamide a) 2-{3-[2-(Tetrahydro-pyran-2-yloxy)-ethyl]-phenyl}-3H-imidazo[4,5-b]pyridine-6-ylamine was prepared as described for example 2-1 starting from 5-bromo-2,3-diaminopyridine and 3-[2-(Tetrahydro-pyran-2-yloxy)-ethyl]-benzaldehyde.

b) 2-Chloro-N-{2-[3-(2-hydroxy-ethyl)-phenyl]-3H-imidazo[4,5-b]pyridin-6-yl}-benzamide 210 mg (0.62 mmol) 2-{3-[2-(Tetrahydro-pyran-2-yloxy)-ethyl]-phenyl}-3H-imidazo[4,5-b]pyridin-6-ylamine were dissolved in 2 ml dry N-methylpyrrolidone (NMP) and cooled to 0 C. 200 mg 2-chlorobenzoylchloride (0.683 mmol) were added and stirring was continued for 10 min at 0 C and for further 3 hrs at room temperature. The solvents were removed under vacuum and the residue taken up in 3 ml methanol and 1 ml conc. aqueous ammonia. The mixture was stirred for 1 hr at room temperature before it was evaporated. The residue was purified by chromatography on silica in ethyl acetate methanol mixtures, yielding 53 mg of the deprotected hydroxyethyl title compound.

$^1$H-NMR (400 MHz, d$^6$-DMSO): δ=10.80 (broad s) and 10.60 (broad s, together 1H); 8.59-8.44 (m, 2H); 8.07 (m, 2H); 7.68-7.40 (m, 6H); 4.72 (s, 1H, exchanges with D2O); 3.71 (m, 2H); 2.85 (s, 2H).

Example 5-1

3-[6-(2-Chloro-benzoylamino)-3H-imidazo[4,5-b]pyridine-2-yl]-benzoic acid a) 3-(6-Nitro-3H-imidazo[4,5-b]pyridin-2-yl)-benzoic acid 0.87 g 3-carboxybenzaldehyde and 0.866 g 2,3-diamino-5-nitropyridine in 50 ml nitrobenzene were heated to 160° C. for 30 hrs. The mixture was cooled to room temperature and 200 ml ethyl acetate and 100 ml ethyl ether were added. The precipitated product was collected by filtration and dried. Yield 1.135 g b) 3-(6-Amino-3H-imidazo[4,5-b]pyridin-2-yl)-benzoic acid 620 mg nitro compound from example 5-1a) were hydrogenated over 0.2 g 10% palladium on charcoal in a mixture of 10 ml tetrahydrofuran (THF) and 70 ml methanol at room temperature. After 5 hrs the catalyst was filtered off over a small pad of silica, and the silica washed with diluted aqueous HCl. The filtrates were evaporated under vacuum to yield 616 mg of the title product as hydrochloride salt.

3-[6-(2-Chloro-benzoylamino)-3H-imidazo[4,5-b]pyridine-2-yl]-benzoic acid 100 mg of the product from example 5-1b) in 2 ml dry NMP were treated at 0° C. with 72 mg 2-chlorobenzoyl chloride. After 30 min the mixture was warmed to room temperature and stirred for another hr. A solution of 25 mg potassium hydroxide in 0.5 ml water was added and stirring was continued for 1 hr. The solvents were removed under vacuum and the residue dissolved in a solution of 2.5 g sodium hydroxide in 100 ml water. The aqueous mixture was washed with dichloromethane, adjusted to pH 1-2 and extracted first with dichloromethane and then with ethyl acetate. The combined extracts were evaporated, dispersed in a mixture of 10 ml methanol+10 ml dichloromethane+10 ethyl acetate, and filtered. The filtrate was evaporated to yield 110 mg of the title product.

$^1$H-NMR (400 MHz, d$^6$-DMSO): δ=13.38 (broad s; 1H); 10.94 (s) and 10.44 (s, together 1H); 8.86 (s, 1H); 8.67 (s, 1H); 8.58 (d, 2H); 8.10 (d, 1H); 7.79-7.43 (m, 5H).

Example 6-1

3-(6-(2-chlorobenzoylamino)-3H-imidazo[4,5-b]pyridine-2-yl)-N-(3-methoxy-propyl)-benzamide 35 mg of the acid from example 5 in 0.75 ml dry DMF were treated with 18 mg carbonyl diimidazole at room temperature. After 1 hr 12 mg 3-methoxypropyl amine were added and stirring continued for 4 hrs. 5 ml water were added and the solvents evaporated under vacuum. The residue was dissolved in a solution of 0.5 g sodium hydroxide in 50 ml water and washed with dichloromethane. The aqueous phase was adjusted to pH 2 with HCl and extracted several times with dichloromethane. The combined organic phases were washed with conc. aqueous sodium bicarbonate solution, dried and evaporated. Yield 9 mg $^1$H-NMR (400 MHz, d$^6$-DMSO): δ=10.43 (s) and 9.90 (s, together 1H); 8.73 (s, 1H); 8.62 (t, 1H); 8.36 (m, 2H); 8.23 (s, 1H); 7.82 (d, 1H); 7.73-7.47 (m, 5H); 3.43-3.29 (m, 7H); 1.81 (m, 2H).

The following examples were obtained in analogous fashion as described for example 6-1:

Example 7-1

2-Chloro-N—[2-(2-methyl-pyridin-4-yl)-3H-imidazo[4,5-b]pyridine-6-yl]-benzamide a) 6-Bromo-2-(2-methyl-pyridin-4-yl)-3H-imidazo[4,5-b]pyridine 0.30 g 5-bromo-2,3-diaminopyridine and 0.212 g 2-methyl-pyridine-4-carboxylic acid were heated in 3 g polyphosphoric acid at 160° C. with stirring for 16 hrs. The mixture was diluted with water and insoluble components removed by filtration. Water was evaporated from the filtrate and the residue dispersed in pyridine. Again, insoluble components were removed by filtration and the filtrate evaporated. The obtained residue was washed thoroughly with water and dried.

Yield 130 mg.

b) [2-(2-Methyl-pyridin-4-yl)-3H-imidazo[4,5-b]pyridine-6-yl]-amine

Obtained from 7-1a) and ammonia analogous to example 4-1b). Purification by chromatography on silica in methanol/dichloromethane mixtures.

2-Chloro-N-[2-(2-methyl-pyridin-4-yl)-3H-imidazo[4,5-b]pyridine-6-yl]-benzamide 15 mg of the product from example 7-1b) in 0.5 ml dry N-methylpyrrolidone (NMP) were treated with 12.3 mg 2-chlorobenzoyl chloride at 0° C. Stirring was continued at room temperature for 2 hrs before the solvents were evaporated under vacuum. The residue was purified by chromatography on silica in methanol dichloromethane 1:10. Product containing fractions were collected, evaporated and further purified by preparative HPLC-MS.

Yield 8 mg of the title product.

$^1$H-NMR (400 MHz, d$^6$-DMSO): δ=13.80 (broad s) and 13.40 (broad s, together 1H); 10.83 (broad s; 1H); 8.67-8.58 (m, 3H); 8.00 (s, 1H); 7.92 (s, 1H); 7.68-7.45 (m, 4H); 2.60 (s, not separated from DMSO).

The following examples were obtained in analogous fashion as described for example 7-1:

| Example-No. | Systematic Name | $^1$H-NMR |
|---|---|---|
| 6-2 | 3-(6-(2-chlorobenzoylamino)-3H-imidazo[4,5-b]pyridine-2-yl)-N-isopropyl-benzamide | (400 MHz, d$^6$-DMSO): δ = 10.79 (s) and 10.70 (s, together 1H); 8.68 (s, 1H); 8.59 (s, 1H); 8.30 (m, 3H); 7.99 (d, 1H); 7.68-7.37 (m, 5H); 4.17 (m, 1H); 1.22 (d, 6H). |
| 6-3 | 2-Chloro-N-(2-{3-[2-methoxy-1-methoxymethyl-ethylcarbamoyl]-phenyl}-3H-imidazo[4,5-b]pyridin-6-yl)-benzamide | (400 MHz, d$^6$-DMSO): δ = 10.80 (broad s, 1H); 8.70 (s, 1H); 8.59 (s) and 8.52 (broad s, together 3H); 8.32 (d, 1H); 8.00 (d, 1H); 7.68 (m, 2H); 7.62 (d, 1H); 7.58-7.48 (m, 2H); 4.38 (m, 1H); 3.50 (m, 4H); 3.30 (s, not separated from H2O). |

| Example-No. | Systematic Name | $^1$H-NMR |
|---|---|---|
| 7-2 | 2-Chloro-N-[2-(6-methyl-pyridin-3-yl)-3H-imidazo[4,5-b]pyridine-6-yl]-benzamide | (400 MHz, d$^6$-DMSO): δ = 13.66 (s) and 13.20 (s, together 1H); 10.83 (s) and 10.71 (s, together 1H); 9.24 (d, 1H); 8.59 (d, 1H); 8.47-8.40 (m, 2H); 7.68-7.46 (m, 5H); 2.57 (s, not separated from DMSO). |
| 7-3 | 2-Chloro-N-[2-(3-methylsulfanyl-phenyl)-3H-imidazo[4,5-b]pyridine-6-yl]-benzamide | (400 MHz, d$^6$-DMSO): δ = 13.55 (broad s) and 13.13 (broad s, together 1H); 10.80 (broad s) and 10.68 (broad s, together 1H); 8.62-8.42 (m, 2H); 8.09 (broad d, 1H); 7.99 (broad s, 1H); 7.60 (d, 1H); 7.55 (d, 1H); 7.52-7.49 (m, 3H); 7.43 (d, 1H); 2.58 (s, 3H). |
| 7-4 | 2-Chloro-N-[2-(4-sulfamoyl-phenyl)-3H-imidazo[4,5-b]pyridine-6-yl]-benzamide | (400 MHz, CD$_3$OD): δ = 8.65 (broad s and 8.57 (broad s, together 2H); 8.24 (d, 2H); 8.03 (d, 2H); 7.64 (d, 1H); 7.61-7.38 (m, 3H). |
| 7-5 | N-[2-(1H-Benzoimidazol-5-yl)-3H-imidazo[4,5-b]pyridine-6-yl]-2-chloro-benzamide | (400 MHz, CD$_3$OD): δ = 8.63 (s, 1H); 8.53 (s) and 8.48 (s, together 2H); 8.35 (s, 1H); 8.13 (d, 1H); 7.81 (d, 1H); 7.67-7.34 (m, 4H). |
| 7-6 | 2-Chloro-N-[2-(4-nitro-phenyl)-3H-imidazo[4,5-b]pyridine-6-yl]-benzamide | (400 MHz, d$^6$-DMSO): δ = 10.98 (broad s, 1H); 8.77 (s) and 8.73 (s, together 1H); 8.59 (m, 3H); 7.87-7.63 (m, 6H). |
| 7-7 | 2-Chloro-N-[2-(6-morpholin-4-yl-pyridin-3-yl)-3H-imidazo[4,5-b]pyridine-6-yl]-benzamide | (400 MHz, d$^6$-DMSO): δ = 10.76 (s) and 10.65 (s, together 1H); 8.93 (d, 1H); 8.51 (t, 1H); 8.36 (s, 1H); 8.28 (dd, 1H); 7.67-7.43 (m, 4H); 7.03 (t, 1H); 3.72 (s, 4H); 3.61 (s, 4H). |

Example 8-1

2-Chloro-N-[2-(4-methylsulfanyl-phenyl)-3H-imidazo[4,5-b]pyridine-6-yl]-benzamide a) 2-(4-Methylsulfanyl-phenyl)-6-nitro-3H-imidazo[4,5-b]pyridine 1.0 g 2,3-diamino-5-nitropyridine and 1.125 g 4-methylsulfanylbenzoic acid in 20 ml polyphosphoric acid were heated to 160° C. with stirring for 15 hrs. The mixture was cooled and poured into water. The pH was adjusted to 4-5 by addition of sodium hydroxide and the precipitate collected by filtration. The filtration residue was stirred in 50 ml pyridine at 60° C., cooled and insoluble components removed by filtration. The filtrate was evaporated and the residue used without further purification in the next steps. Yield 0.656 g of 30% purity b) 2-(4-Methylsulfanyl-phenyl)-3H-imidazo[4,5-b]pyridine-6-ylamine 0.656 g of the nitro compound from example 8-1a) and 0.326 g of powdered tin were suspended in a mixture of 20 ml water and 10 ml conc. HCl and stirred at 80° C. After 3 hrs the mixture was cooled to room temperature, diluted with 50 ml methanol and filtered. The filtrate was further diluted with 50 ml water and adjusted to pH ~12 by addition of ammonia. Resulting precipitate was again filtered off over a small pad of silica, and the filtrate was evaporated. The residue was dissolved in methanol/dichloromethane 2:1 and filtered once more over a pad of silica. The filtrate was finally evaporated and the residue used as such without further purification for the next step. Yield 195 mg of 60% purity 2-Chloro-N-[2-(4-methylsulfanyl-phenyl)-3H-imidazo[4,5-b]pyridine-6-yl]-benzamide 150 mg of the product from example 8-1b) in 1.5 ml dry N-methylpyrrolidone (NMP) were cooled in an ice bath. 105 mg 2-chlorobenzoyl chloride were added and the mixture was stirred 30 min with cooling, then another 2 hrs at room temperature. 0.5 ml conc. ammonia were added and stirring was continued for another 20 min. The solvents were removed under vacuum and the residue was purified by chromatography on silica, eluting first with dichloromethane, then with methanol/dichloromethane 1:40. Yield 43 mg $^1$H-NMR (400 MHz, d$^6$-DMSO): δ=13.51 (broad s) and 13.17 (broad s, together 1H); 10.80 (s) and 10.68 (s, together 1H); 8.57 (s) and 8.53 (s) and 8.42 (s, together 2H); 8.42 (d) and 8.12 (d, together 1H); 7.67-7.42 (m, 6H); 2.57 (s, 3H).

Example 9-1

2-Chloro-N-[2-(3-methanesulfinyl-phenyl)-3H-imidazo[4,5-b]pyridine-6-yl]-benzamide 110 mg meta-chloro perbenzoic acid (m-CPBA) (70%) were dissolved in 20 ml dichloromethane and dried by filtration over magnesium sulfate. 2 ml of this solution (=11 mg m-CPBA) were added to a suspension of 21 mg of the product from ex. 7-3 in 2 ml dichloromethane at 4° C. After 30 min the temperature was raised to room temperature and stirring was continued for another 60 min. The solvent was removed and the residue chromatographed on silica, eluting first with dichloromethane and then with dichloromethane/methanol/conc. ammonia 40:2:1. Yield 6 mg $^1$H-NMR (400 MHz, d$^6$-DMSO): δ=10.84 (s) and 10.73 (s, together 1H); 8.62-8.50 (m, 3H); 8.35 (broad s, 1H); 7.83 (m, 2H); 7.67 (d, 1H); 7.63-7.49 (m, 3H); 2.85 (s, 3H).

Example 9-2

2-Chloro-N-[2-(4-methanesulfonyl-phenyl)-3H-imidazo[4,5-b]pyridine-6-yl]-benzamide 36 mg 2-Chloro-N-[2-(4-methanesulfanyl-phenyl)-3H-imidazo[4,5-b]pyridine-6-yl]-benzamide and 55 mg Oxone in a mixture of 1.5 ml methanol, 0.2 ml water and 0.2 ml dimethylformamide were stirred at room temperature for 2 hrs. Water was added and the crude product isolated by filtration and further purified by chromatography on silica, eluting first with dichloromethane, then with dichloromethane/methanol 30:1. Yield 10 mg $^1$H-NMR (400 MHz, d$^6$-DMSO): δ=10.85 (broad s) and 10.73 (broad s, together 1H); 8.62 (broad s) and 8.55 (broad s, together 2H); 8.45 (broad s, 2H); 8.14 (d, 2H); 7.67 (d, 1H); 7.61 (d, 1H); 7.58-7.49 (m, 2H); 2.53 (s, not separated from DMSO).

Example 10-1

N-[2-(3-Amino-phenyl)-3H-imidazo[4,5-b]pyridine-6-yl]-2-chloro-benzamide 50 mg of the nitro-phenyl derivative from example 4-4 in 3 ml tetrahydrofuran (THF) and 3 ml methanol were hydrogenated over 20 mg 10% Pd on charcoal at room temperature for 45 min (42 mbar) The catalyst was filtered off and washed with methanol. The filtrate was evaporated and the residue purified by chromatography on C-18 RP silica in methanol/water mixtures. Yield 20 mg $^1$H-NMR (400 MHz, D$_6$-DMSO): δ=13.05 (broad s; 1H); 10.89 (broad s) and 10.62 (broad s, together 1H); 8.76 (s) and 8.67 (s) and 8.61 (broad s, together 2H); 7.81-7.55 (m, 4H); 7.46 (broad s; 1H); 7.36 (t, 1H); 6.87 (d, 1H); 5.49 (broad s, 2H).

Example 11-1

N-[2-(3-Acetylamino-phenyl)-3H-imidazo[4,5-b]pyridine-6-yl]-2-chloro-benzamide 10 mg of the product from example 10-1 were dissolved in 1 ml dry pyridine and 6 μl acetyl chloride were added at room temperature. After stirring over night, the solvent was evaporated and the residue dissolved in 3 ml methanol. 1 ml conc. ammonia were added and the mixture stirred for 1 hr at room temperature. The solvents were again evaporated and the residue purified by chromatography on C-18 RP silica in water methanol mixtures. Yield 7.3 mg $^1$H-NMR (400 MHz, d$^6$-DMSO): δ=13.22 (broad s; 1H); 10.75 (broad s) and 10.49 (broad s, together 1H); 10.17 (s, 1H); 8.65 (s) and 8.55 (s, together 2H); 8.51 (s, 2H); 7.83 (d, 1H); 7.73-7.47 (m; 6H); 2.10 (s, 3H).

Example 12-1

2-Chloro-N-(2-phenyl-1H-pyrrolo[2,3-b]pyridine-5-yl)-benzamide a) 5-Nitro-3-phenylethynyl-pyridin-2-ylamine 1.83 g 2-amino-3-bromo-5-nitropyridine 0.29 g PdCl2 (PPh3)2 and 79 mg CuI were mixed in 36 ml dry tetrahydrofuran (THF) and 3.45 ml triethylamine and 1.12 g phenylacetylene were added. Stirring was continued at room temperature for 12 hrs, then the solvent was removed and the residue purified by flash chromatography on silica in ethyl acetate/heptane eluent. Yield 855 mg.

b) 5-Nitro-2-phenyl-1H-pyrrolo[2,3-b]pyridine 0.843 g potassium tert. butylate in 15 ml dry N-methylpyrrolidone (NMP) were treated with a solution of 0.855 g of the product from example 12-1a) in 15 ml NMP. The mixture was stirred at room temperature for 12 hrs, then transferred onto a short column of ca. 150 g silica. The product was eluted sequentially with heptane, then heptane/ethyl acetate 1:1. Product containing fractions were collected and evaporated, and the residue dispersed in water. Filtration and washing of the filter residue with water and heptane yielded 0.55 g of the title product.

c) 2-Phenyl-1H-pyrrolo[2,3-b]pyridine-5-ylamine 200 mg of the product from example 12-1b) in 15 ml methanol were hydrogenated over 40 mg 10% Pd on charcoal at room temperature for 2.5 hrs. The mixture was filtered and the product purified by chromatography on C-18 RP silica in methanol water. Yield 107 mg

2-Chloro-N-(2-phenyl-1H-pyrrolo[2,3-b]pyridine-5-yl)-benzamide 109 mg of the product from example 12-1c) were dissolved in 4 ml dry Pyridine. 272 mg 2-chlorobenzoyl chloride were added at room temperature and the mixture was stirred for 16 hrs. The solvent was evaporated and the residue stirred with 3 ml methanol and 1 ml conc. ammonia for 1 hr at room temperature. Finally the solvents were removed under vacuum and the residue purified by chromatography on silica. Product containing fractions were collected and further purified by preparative HPLC-MS. Yield 13 mg.

$^1$H-NMR (400 MHz, CD$_3$OD): δ=8.40 (s) and 8.38 (s, together 2H); 7.88 (d, 2H); 7.69-7.35 (m, 7H); 6.89 (s; 1H).

Example 12-2

2-Chloro-N-[2-[3-(2-methoxy-ethoxy)-phenyl]-1H-pyrrolo[2,3-b]pyridine-5-yl]-benzamide a) 3-[3-(2-methoxy-ethoxy)-phenylethynyl]-5-nitro-pyridin-2-ylamine 3-(2-Methoxy-ethoxy)-phenylacetylene (6.3 g, 36 mmol) was added to a solution of triethylamine (1.92 mL, 14 mmol), 2-amino-3-bromo-5-nitropyridine (4 g, 18 mmol), PdCl$_2$ (PPh$_3$)$_2$ (966 mg, 1.38 mmol) and CuI (262 mg, 1.38 mmol) in anhydrous tetrahydrofuran (80 mL) in the dark. The mixture was stirred at room temperature for 48 hours then concentrated in vacuo and dissolved in dichloromethane (150 mL). The organic solution was washed with water (25 mL), dried over MgSO$_4$, filtered and concentrated in vacuo to 20% of its original volume and heptane (20 mL) was then added. The resultant yellow solid was filtered and dried to give 3-[3-(2-methoxy-ethoxy)-phenylethynyl]-5-nitro-pyridin-2-ylamine (4.2 g, 74% yield).

$^1$H-NMR (400 MHz; d$^6$-DMSO): δ=8.89 (1H, d, J 2.7), 8.34 (1H, d, J 2.7), 7.39 (1H, m), 7.35 (1H, d, J 8.0), 7.30 (1H, dt, J 1.0, 7.6), 7.04 (1H, ddd, J 1.0, 2.6, 8.2), 4.15 (2H, t, J 4.5), 3.69 (2H, t, J 4.5), 3.34 (3H, s).

MS: M=(ES+) 314 (M+H), 355 (M+acetonitrile)

b) 2-[3-(2-methoxy-ethoxy)-phenyl]-5-nitro-1H-pyrrolo[2,3-b]pyridine

Potassium tert-butoxide (1.18 g, 10.5 mmol) was added to a solution of 3-[3-(2-methoxy-ethoxy)-phenylethynyl]-5-nitro-pyridin-2-ylamine (1.57 g, 5 mmol) in a 2:1 mixture of tetrahydrofuran and dimethylformamide (75 mL). The mixture was heated at 70° C. for 16 hours then the tetrahydrofuran was removed in vacuo. The mixture was poured onto a pad of silica and eluted with ethyl acetate then 10% methanol in ethyl acetate. The organics were concentrated in vacuo to 5% of their original volume and water (30 mL) was added. The resultant orange solid was filtered and dried to afford 2-[3-(2-methoxy-ethoxy)-phenyl]-5-nitro-1H-pyrrolo[2,3-b]pyridine (1.3 g, 83%).

$^1$H-NMR (400 MHz; d$^6$-DMSO): δ=12.88 (1H, s), 9.04 (1H, d, J 2.6), 8.77 (1H, d, J 2.6), 7.52-7.50 (2H, m), 7.36 (1H, app. t, J 8.1, 7.8), 7.18 (1H, s), 6.95 (1H, dd, J 1.8, 8.1), 4.15 (2H, t, J 4.6), 3.65 (2H, t, J 4.6), 3.25 (3H, s).

MS: M=(ES+) 314 (M+H), 355 (M+acetonitrile)

c) 2-[3-(2-methoxy-ethoxy)-phenyl]-1H-pyrrolo[2,3-b]pyridin-5-ylamine

To a mixture of 2-[3-(2-methoxy-ethoxy)-phenyl]-5-nitro-1H-pyrrolo[2,3-b]pyridine (7.1 mmol, 2.2 g) and iron powder (6.7 g) in ethanol (50 mL) was added HCl (conc.) (0.7 mL) and water (5 mL). The mixture was heated at 70° C. for 3 hours then cooled and filtered through Celite®. The solvent was removed in vacuo and the residue dissolved in ethyl acetate (30 mL), washed with saturated sodium bicarbonate (15 mL), dried over MgSO$_4$, filtered and concentrated in vacuo. The crude product was purified by column chromatography (SiO$_2$, ethyl acetate) to afford 2-[3-(2-methoxy-ethoxy)-phenyl]-1H-pyrrolo[2,3-b]pyridin-5-ylamine (1.2 g, 60%).

$^1$H-NMR (400 MHz; d$^6$-DMSO): δ=11.62 (1H, s), 7.78 (1H, d, J 2.0), 7.53-7.50 (2H, m), 7.38 (1H, app. t, J 8.0), 7.13 (1H, d, J 2.3), 6.93 (1H, dd, J 1.7, 8.0), 6.75 (1H, d, J 2.0), 4.8 (2H, br.s), 4.24 (2H, t, J 4.6), 3.76 (2H, t, J 4.6), 3.40 (3H, s).

MS: M=(ES+) 284 (M+H)

2-Chloro-N-{2-[3-(2-methoxy-ethoxy)-phenyl]-1H-pyrrolo[2,3-b]pyridine-5-yl}-benzamide The above amino compound was acylated with 2-chlorobenzoylchloride as described for example 12-1 to yield the title compound.

$^1$H-NMR (400 MHz, d$^6$-DMSO): δ=12.12 (s, 1H); 10.56 (s, 1H); 8.44 (s, 1H); 8.37 (s, 1H); 7.68-7.45 (m, 6H); 7.38 (t, 1H); 7.00 (s; 1H); 6.94 (s, 1H); 4.21 (t, 2H); 3.72 (t, 2H).

The following examples were obtained in analogous fashion as described for example 12-2:

| Example-No. | Systematic Name | $^1$H-NMR |
|---|---|---|
| 12-3 | 2-Methoxy-N-(2-phenyl-1H-pyrrolo[2,3-b]pyridine-5-yl)-benzamide | (400 MHz, d$^6$-DMSO): δ = 10.23 (s, 1H); 8.51 (broad s, 1H); 8.46 (s, 1H); 7.97 (d, 2H); 7.72 (d, 1H); 7.58-7.46 (m, 3H); 7.38 (t, 1H); 7.22 (d, 1H); 7.10 (t, 1H); 7.00 (s, 1H); 3.95 (s, 3H). |
| 12-4 | 2,4-Dichloro-N-(2-phenyl-1H-pyrrolo[2,3-b]pyridine-5-yl)-benzamide | (400 MHz, d$^6$-DMSO): δ = 11.95 (s, 1H); 10.39 (s, 1H); 8.20 (s, 1H); 8.14 (s, 1H); 7.74 (d, 2H); 7.59 (s, 1H); 7.48 (d, 1H); 7.38 (d, 1H); 7.27 (t, 2H); 7.15 (t, 1H); 6.76 (s, 1H). |
| 12-5 | 2-Chloro-6-methyl-N-(2-phenyl-1H-pyrrolo[2,3-b]pyridine-5-yl)-benzamide | (400 MHz, d$^6$-DMSO): δ = 12.25 (s, 1H); 10.69 (s, 1H); 8.49 (s, 1H); 8.44 (s, 1H); 8.03 (d, 2H); 7.57 (t, 2H); 7.50-7.39 (m, 4H); 7.05 (s, 1H); 2.46 (s, 3H). |
| 12-6 | N-[2-(3-Acetylamino-phenyl)-1H-pyrrolo[2,3-b]pyridine-5-yl]-4-methoxy-benzamide | (400 MHz, d$^6$-DMSO): δ = 12.08 (s, 1H); 10.17 (s, 1H); 10.07 (s, 1H); 8.47 (s, 1H); 8.33 (s, 1H); 8.10 (s, 1H); 8.01 (d, 2H); 7.60 (d, 1H); 7.54 (d, 1H); 7.40 (t, 1H); 7.09 (d, 2H); 6.78 (s, 1H); 3.86 (s, 3H); 2.09 (s, 3H). |
| 12-7 | 2-Methyl-N-(2-phenyl-1H-pyrrolo[2,3-b]pyridine-5-yl)-benzamide | (400 MHz, d$^6$-DMSO): δ = 11.92 (s, 1H); 10.14 (s, 1H); 8.26 (s, 1H); 8.19 (s, 1H); 7.76 (s) and 7.74 (s, together 2H); 7.33-7.26 (m, 3H); 7.23-7.11 (m, 4H); 6.76 (s, 1H); 2.23 (s, 3H). |
| 12-8 | 2-Chloro-5-methoxy-N-{2-[3-(2-methoxy-ethoxy)-phenyl]-1H-pyrrolo[2,3-b]pyridine-5-yl}-benzamide | |
| 12-9 | 2,4-Dichloro-N-{2-[3-(2-methoxy-ethoxy)-phenyl]-1H-pyrrolo[2,3-b]pyridine-5-yl}-benzamide | (400 MHz, d$^6$-DMSO): δ = 12.28 (s, 1H); 10.75 (s, 1H); 8.56 (s, 1H); 8.50 (s, 1H); 7.95 (s, 1H);) 7.84 (d, 1H); 7.74 (d, 1H); 7.68 (dd, 2H); 7.52 (t, 1H); 7.15 (s, 1H); 7.08 (d, 1H); 4.35 (t, 2H); 3.86 (t, 2H); 3.49 (not separated from H2O). |
| 12-10 | 4-Methoxy-N-{2-[3-(2-methoxy-ethoxy)-phenyl]-1H-pyrrolo[2,3-b]pyridine-5-yl}-benzamide | (400 MHz, d$^6$-DMSO): δ = 11.99 (s, 1H); 10.09 (s, 1H); 8.40 (s, 1H); 8.24 (s, 1H); 7.94 (d, 2H);) 7.47 (m, 2H); 7.30 (s, 1H); 7.02 (d, 2H); 6.91 (s, 1H); 6.85 (d, 1H); 4.13 (t, 2H); 3.79 (s, 3H); 3.64 (t, 2H); 3.27 (not separated from H2O). |
| 12-11 | 3,5-Dimethoxy-N-{2-[3-(2-methoxy-ethoxy)- | (400 MHz, d$^6$-DMSO): δ = 12.09 (s, 1H); 10.26 (s, 1H); 8.47 (s, 1H); 8.31 (s, 1H); |

-continued

| Example-No. | Systematic Name | $^1$H-NMR |
|---|---|---|
| | phenyl]-1H-pyrrolo[2,3-b]pyridine-5-yl}-benzamide | 7.55 (broad s) and 5.52 (s, together 2H); 7.38 (t, 1H); 7.16 (s, 2H); 6.99 (s, 1H); 6.94 (d, 1H); 6.74 (t, 1H); 4.21 (t, 2H); 3.85 (s, 6H); 3.72 (t, 2H); 3.35 (s, not separated from H$_2$O). |
| 12-12 | 3,5-Dimethoxy-N-(2-phenyl-1H-pyrrolo[2,3-b]pyridine-5-yl)-benzamide | (400 MHz, d$^6$-DMSO): δ = 12.13 (s, 1H); 10.26 (s, 1H); 8.48 (s, 1H); 8.31 (s, 1H); 7.96 (d, 2H); 7.49 (t, 2H); 7.36 (t, 1H); 7.16 (s, 2H); 6.96 (s, 1H); 6.74 (t, 1H); 3.85 (s, 6H). |
| 12-13 | N-{2-[3-(2-Methoxy-ethoxy)-phenyl]-1H-pyrrolo[2,3-b]pyridine-5-yl}-2-methyl-benzamide | (400 MHz, d$^6$-DMSO): δ = 12.13 (s, 1H); 10.38 (s, 1H); 8.50 (s, 1H); 7.59-7.55 (m, 3H); 7.48-7.35 (m, 4H); 7.02 (s, 2H); 6.97 (d, 1H); 4.25 (t, 2H); 3.76 (t, 2H); 3.36 (s, not separated from H2O); 2.47 (s, 3H). |
| 12-14 | 2-Methoxy-N-{2-[4-(2-methoxy-ethoxy)-phenyl]-1H-pyrrolo[2,3-b]pyridin-5-yl}-benzamide | (400 MHz, CD$_3$OD): δ = 8.49 (s, 1H); 8.44 (s, 1H); 8.09 (d, 1H); 7.94 (d, 2H); 7.70 (t, 1H); 7.36 (d, 1H); 7.26 (t, 1H); 7.20 (d, 2H); 6.88 (s, 1H); 4.33 (t, 2H); 4.20 (s, 3H); 3.92 (t, 2H); 3.59 (s, 3H). |

Example 12-15

N-[2-(3-Acetylamino-phenyl)-1H-pyrrolo[2,3-b]pyridine-5-yl]-2-chloro-benzamide was prepared analogously to example 12-2 starting from 3-(acetylamino)phenylacetylene. In the preparation of the intermediate N-[3-(5-nitro-1H-pyrrolo[2,3-b]pyridin-2-yl)-phenyl]-acetamide by cyclisation reaction an higher equimolar amount of base (potassium tert-butoxide) as in Example 12-2 is needed:

Preparation of N-[3-(5-nitro-1H-pyrrolo[2,3-b]pyridin-2-yl)-phenyl]-acetamide

Potassium tert-butoxide (2.25 g, 20 mmol) was added to a solution of N-[4-(2-amino-5-nitro-pyridin-3-ylethynyl)-phenyl]-acetamide (1.48 g, 5 mmol) in a 2:1 mixture of tetrahydrofuran and dimethylformamide (75 mL). The mixture was heated at 70° C. for 16 hours then the tetrahydrofuran was removed in vacuo. The mixture was poured onto a pad of silica and eluted with 10% methanol in ethyl acetate. The organics were concentrated in vacuo to 5% of their original volume and water (30 mL) was added. The resultant orange solid was filtered and dried to afford N-[3-(5-Nitro-1H-pyrrolo[2,3-b]pyridin-2-yl)-phenyl]-acetamide (1.01 g, 68%).

$^1$H-NMR (400 MHz; d$^6$-DMSO): δ=12.97 (1H, s), 10.17 (1H, s), 9.16 (1H, d, J 2.5), 8.94 (1H, d, J 2.5), 8.24 (1H, s), 7.70 (1H, d, J 7.8), 7.63 (1H, d, J 8.2), 7.50 (1H, app. t, J 7.9), 7.10 (1H, s), 2.15 (3H, s).

MS: M=(ES+) 297 (M+H), 338 (M+acetonitrile), 593 (2M+H), 889 (3M+H)

N-[2-(3-Acetylamino-phenyl)-1H-pyrrolo[2,3-b]pyridine-5-yl]-2-chloro-benzamide

The above nitro compound was reduced to the amino compound and subsequently acylated with 2-chlorobenzoylchloride as described in example 9-1 to yield the title compound.

$^1$H-NMR (400 MHz, d$^6$-DMSO): 3=12.14 (s, 1H); 10.56 (s, 1H); 10.07 (s, 1H); 8.41 (s, 2H); 8.09 (s, 1H); 7.67-7.37 (m, 7H); 6.81 (s, 1H); 2.09 (s, 3H).

The following examples were obtained in analogous fashion as described for example 12-15:

| Example-No. | Systematic Name | $^1$H-NMR |
|---|---|---|
| 12-16 | N-[2-(3-Acetylamino-phenyl)-1H-pyrrolo[2,3-b]pyridin-5-yl]-2,4-dichloro-benzamide | (400 MHz, d$^6$-DMSO): δ = 12.24 (s, 1H); 10.69 (s, 1H); 10.16 (s, 1H); 8.48 (d, 2H); 8.18 (s, 1H); 7.89 (s, 1H); 7.78 (d, 1H); 7.70-7.66 (m, 2H); 7.63 (d, 1H); 7.49 (t, 1H); 6.96 (d, 1H); 2.18 (s, 3H). |
| 12-17 | N-[2-(3-Acetylamino-phenyl)-1H-pyrrolo[2,3-b]pyridin-5-yl]-2-methoxy-benzamide | (400 MHz, d$^6$-DMSO): δ = 12.11 (s, 1H); 10.17 (s, 1H); 10.07 (s, 1H); 8.43 (m, 2H); 8.09 (s, 1H); 7.72 (d, 1H); 7.71-7.56 (m, 3H); 7.70 (t, 1H); 7.21 (d, 1H); 7.10 (t, 1H); 6.79 (s, 1H); 3.95 (s, 3H); 2.10 (s, 3H). |
| 12-18 | N-[2-(3-Acetylamino-phenyl)-1H-pyrrolo[2,3-b]pyridin-5-yl]-2-chloro-6-methyl-benzamide | (400 MHz, d$^6$-DMSO): δ = 12.28 (s, 1H); 10.73 (s, 1H); 10.19 (s, 1H); 8.51 (s, 2H); 8.20 (s, 1H); 7.72 (d, 1H); 7.68 (d, 1H); 7.55-7.49 (m, 3H); 7.44 (m, 1H); 6.93 (s, 1H); 2.49 (s, 3H); 2.21 (s, 3H). |

-continued

| Example-No. | Systematic Name | ¹H-NMR |
|---|---|---|
| 12-19 | N-[2-(3-Acetylamino-phenyl)-1H-pyrrolo[2,3-b]pyridin-5-yl]-2-chloro-5-methoxy-benzamide | (400 MHz, d⁶-DMSO): δ = 11.99 (s, 1H); 10.39 (s, 1H); 9.93 (s, 1H); 8.27 (d, 2H); 7.95 (s, 1H); 7.46 (d, 1H); 7.41 (d, 1H); 7.35 (d, 1H); 7.27 (t, 1H); 7.08 (s, 1H); 6.96 (d, 1H); 6.67 (s, 1H); 3.70 (s, 3H); 1.95 (s, 3H). |

Example 13-1

N-(2-{4-[Bis-(2-methoxy-ethyl)-amino]-3-fluoro-phenyl}-3H-imidazo[4,5-b]pyridin-6-yl)-2-chloro-benzamide a) 2-(3,4-Difluoro-phenyl)-6-nitro-3H-imidazo[4,5-b]pyridine 1.00 g 2,3-diamino-5-nitro-pyridine and 0.95 g 3,4-difluorobenzaldehyde were stirred in 60 ml nitrobenzene at 160 C for 26 hrs. The solvent was removed under vacuum and the residue dissolved in 40 ml pyridine at 60 C. The solution was cooled in an ice bath. Precipitated product was isolated by filtration and dried to yield 0.5 g of the title product.

b) [2-Fluoro-4-(6-nitro-3H-imidazo[4,5-b]pyridin-2-yl)-phenyl]-bis-(2-methoxy-ethyl)-amine 0.5 g 2-(3,4-Difluoro-phenyl)-6-nitro-3H-imidazo[4,5-b]pyridine, 0.1 ml NMP and 0.51 g bis(2-methoxyethyl)-amine were heated to 170 C with stirring for 18 hrs. Volatile materials were removed under vacuum and the residue purified by chromatography, first on silica in dichloromethane/methanol mixtures, and subsequently by preparative HPLC.

Yield 42 mg of the title product

N-(2-{4-[Bis-(2-methoxy-ethyl)-amino]-3-fluoro-phenyl}-3H-imidazo[4,5-b]pyridin-6-yl)-2-chloro-benzamide The above nitro compound was hydrogenated to the amino compound and subsequently acylated with 2-chlorobenzoyl-chloride as described for 4-9 to give the title product.

¹H-NMR (400 MHz, d⁶-DMSO): δ=10.77 (s) and 10.66 (s, together 1H); 8.54-8.47 (t, 2H); 8.37 (s, 1H); 7.91-7.80 (m, 2H); 7.66 (d, 1H); 7.60 (d, 1H); 7.55-7.48 (m, 2H); 7.17 (m, 1H); 3.53 (m, 8H); 3.25 (s, 6H).

(400 MHz, CD₃OD): δ=8.27 (broad s, 2H); 7.79 (m, 2H); 7.14 (t, 1H); 5.02 (m, 1H); 3.61 (m, 8H); 3.35 (s, not separated from MeOH); 1.35 (d, 6H).

Example 14-1

2-Chloro-N-{2-[2-(3-methoxy-propylamino)-pyridin-4-yl]-3H-imidazo[4,5-b]pyridin-6-yl}-benzamide a) 2-(2-Chloro-pyridin-4-yl)-6-nitro-3H-imidazo[4,5-b]pyridine was prepared as described for example 8-1, starting from 2-chloropyridine-4-carboxylic acid and 2,3-diamino-5-nitro-pyridine.

b) (3-Methoxy-propyl)-[4-(6-nitro-3H-imidazo[4,5-b]pyridin-2-yl)-pyridin-2-yl]-amine 1.20 g (4.35 mmol) 2-(2-Chloro-pyridin-4-yl)-6-nitro-3H-imidazo[4,5-b]pyridine in 12 ml dry N-methylpyrrolidone (NMP) and 1.18 g (13 mmol) 3-methoxypropylamine were heated to 200 C in a closed vessel in a microwave reactor for 30 min. The solvent was removed under vacuum and the residue dissolved in a mixture of 20 ml ethyl acetate and 30 ml 5% aqueous HCl. The HCl phase was separated and brought to alkaline pH by addition of conc. ammonia. The alkaline aqueous phase was extracted with dichloromethane, and the organic phases were combined and dried. Evaporation and chromatography of the residue on silica in ethyl acetate/methanol mixtures gave 480 mg of the title product.

c) 2-[2-(3-Methoxy-propylamino)-pyridin-4-yl]-3H-imidazo[4,5-b]pyridin-6-ylamine The above nitro compound was reduced with iron powder as described in example 1-1 and purified by chromatography on silica in ethyl acetate/methanol mixtures.

Yield 360 mg of the title product

2-Chloro-N-{2-[2-(3-methoxy-propylamino)-pyridin-4-yl]-3H-imidazo[4,5-b]pyridin-6-yl}-benzamide 170 mg (0.57 mmol) of the above amino compound were dissolved in 3 ml NMP and treated dropwise at 0 C with 157 mg (0.85 mmol) 2-chlorobenzoylchloride. Stirring was continued at room temperature for 2 hrs, then methanol and a few ml of conc. ammonia were added and the mixture was stirred for another hr. Evaporation and chromatography on silica in ethyl acetate/methanol mixtures gave 115 mg of the title product.

¹H-NMR (400 MHz, d⁶-DMSO): δ=13.72 (s) and 13.20 (s, together 1H); 10.80 (broad s, 1H); 8.60 (s) and 8.55 (broad s, together 2H); 8.15 (d, 1H); 7.66 (d, 1H); 7.60 (d, 1H); 7.57-7.47 (m, 2H); 7.22 (broad d, 2H); 6.82 (broad s, 1H, exchanges with D₂O); 3.43 (t, 2H); 3.35 (m, not separated from H₂O); 3.26 (s, 3H); 1.81 (m, 2H).

LIST OF REFERENCES

Avizienyte, E., et al., Nature Cell Bio. 4 (2002) 632-638
Bastin, R. J., et al., Organic Proc. Res. Dev. 4 (2000) 427-435
Biscardi, J. S., et al., Adv. Cancer Res. 76 (2000) 61-119
Boyce, B. F., et al., J. Clin., Invest. 90 (1992) 1622-1627
Cai, S. X., et al, J. Med. Chem. 40 (1997) 3679-3686
Eliceiri, B. P., et al., Mol. Cell. 4 (1999) 915-924
Ellis, L. M., et al., J. Biol. Chem. 273 (1998) 1052-1057
Magdolen, P., et al, Tetrahedron 57 (2001) 4781-4785
Missbach, M., et al., Bone 24 (1999) 437-449

Nam, J. S., et al., Clin. Cancer Res. 8 (2002) 2430-2436
Paul, R., et al., Nat. Med. 7 (2001) 222-227
Sawyer, T., et al., Expert Opin. Investig. Drugs 10 (2001) 1327-1344
Schwartzberg, P. L., Oncogene 17 (1998) 1463-1468
Soriano, P., et al., Cell 64 (1991) 693-702
Stahl, P. H., and Wermuth, G., (editors), Handbook of Pharmaceutical Salts, Verlag Helvetica Chimica Acta (VHCA), Zürich (2002)
Staley, C. A., Cell Growth Differ. 8 (1997) 269-274
Susva, M., et al., Trends Pharmacol. Sci. 21 (2000) 489-495
Tsuji, M., J. Org. Chem. 68 (2003) 9589-9597-supporting information S. 1-36-http://pubs.acs.org/subscribe/journals/joceah/suppinfo/jo035090f/jo035 090fsi20030918_025110.pdf.
US 2004/0242883
U.S. Pat. No. 4,162,265A
Weis, S., et al., J. Clin. Invest. 113 (2004) 885-894
WO 01/00213
WO 01/94341
WO 02/016352
WO 02/083668
WO 02/092573
WO 03/004492
WO 03/035065
WO 04/024897
WO 04/041823
WO 04/085436

The invention claimed is:

1. A compound according to formula I,

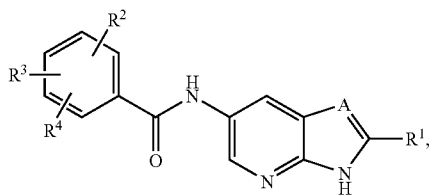

formula I wherein,
R$^1$ is a phenyl group optionally substituted with halogen, cyano, nitro, amino, —C(O)OH, heterocyclyl, —O-heterocyclyl, —S(O)$_2$NH$_2$, —X-alkyl or —Y-cycloalkyl;
or a heteroaryl group optionally substituted with halogen, nitro, amino, heterocyclyl or —Z-alkyl;
and all alkyl groups are optionally substituted one or several times by halogen, hydroxy, alkoxy, amino, alkylamino, dialkylamino or alkylsulfonyl;
X is a single bond, —NR—, —O—, —S—, —CH$_2$—S(O)$_2$ NH—, —NHS(O)$_2$—, —S(O)$_2$NH—, —S(O)$_2$—, —S(O)—, —NRC(O)— or —C(O)NR—;
Y is —NRC(O)— or —C(O)NR—;
Z is a single bond, —NH— or —O—;
R is hydrogen or alkyl, wherein the alkyl is optionally substituted one or several times by halogen or alkoxy;
R$^2$, R$^3$, and R$^4$ independently represent hydrogen, halogen, cyano, nitro, amino, hydroxy, amino, alkoxy, alkylamino, dialkylamino, alkyl, wherein the alkyl and alkoxy groups are optionally substituted one or several times by halogen;
A is =CH— or =N—;
or a pharmaceutically acceptable salt thereof.

2. A compound according to claim 1, wherein
R$^1$ is a phenyl group optionally substituted one to three, preferably one or two, times with halogen, nitro, amino, —C(O)OH, heterocyclyl, —S(O)$_2$NH$_2$ or —X-alkyl;
or a heteroaryl group optionally substituted one or two times with heterocyclyl or —Z-alkyl;
and all alkyl groups are optionally substituted one or two times by hydroxy, alkoxy or dialkylamino;
X is —NR—, —O—, —S—, —S(O)$_2$—, —S(O)—, —NRC(O)— or —C(O)NR—;
Z is a single bond or —NR—;
R is hydrogen or alkyl, wherein the alkyl is optionally substituted one or two times by alkoxy;
R$^2$ and R$^3$ independently represent hydrogen, halogen, nitro, amino, alkoxy or alkyl; and
R$^4$ is hydrogen.

3. A compound according to claim 1, wherein
R$^1$ is a phenyl group optionally substituted one to three, preferably one or two, times with —X-alkyl; and the alkyl group is optionally substituted one or two times by alkoxy;
X is —O— or —NRC(O)—;
R is hydrogen;
R$^2$ and R$^3$ independently represent hydrogen, chlorine, alkoxy or alkyl;
R$^4$ is hydrogen; and
A is =CH—.

4. A compound according to claim 3 selected from the group consisting of:
2-Chloro-N-(2-phenyl-1H-pyrrolo[2,3-b]pyridin-5-yl)-benzamide;
2-Chloro-N-{2-[3-(2-methoxy-ethoxy)-phenyl]-1H-pyrrolo[2,3-b]pyridin-5-yl}-benzamide;
2-Methoxy-N-(2-phenyl-1H-pyrrolo[2,3-b]pyridin-5-yl)-benzamide;
2,4-Dichloro-N-(2-phenyl-1H-pyrrolo[2,3-b]pyridin-5-yl)-benzamide;
2-Chloro-6-methyl-N-(2-phenyl-1H-pyrrolo[2,3-b]pyridin-5-yl)-benzamide;
N-[2-(3-Acetylamino-phenyl)-1H-pyrrolo[2,3-b]pyridin-5-yl]-4-methoxy-benzamide;
2-Methyl-N-(2-phenyl-1H-pyrrolo[2,3-b]pyridin-5-yl)-benzamide;
2-Chloro-5-methoxy-N-{2-[3-(2-methoxy-ethoxy)-phenyl]-1H-pyrrolo[2,3-b]pyridin-5-yl}-benzamide;
2,4-Dichloro-N-{2-[3-(2-methoxy-ethoxy)-phenyl]-1H-pyrrolo[2,3-b]pyridin-5-yl}-benzamide;
4-Methoxy-N-{2-[3-(2-methoxy-ethoxy)-phenyl]-1H-pyrrolo[2,3-b]pyridin-5-yl}-benzamide;
3,5-Dimethoxy-N-{2-[3-(2-methoxy-ethoxy)-phenyl]-1H-pyrrolo[2,3-b]pyridin-5-yl-benzamide;
3,5-Dimethoxy-N-(2-phenyl-1H-pyrrolo[2,3-b]pyridin-5-yl)-benzamide;
N-{2-[3-(2-Methoxy-ethoxy)-phenyl]-1H-pyrrolo[2,3-b]pyridin-5-yl}-2-methyl-benzamide;
2-Methoxy-N-{2-[4-(2-methoxy-ethoxy)-phenyl]-1H-pyrrolo[2,3-b]pyridin-5-yl}-benzamide;
N-[2-(3-Acetylamino-phenyl)-1H-pyrrolo[2,3-b]pyridin-5-yl]-2-chloro-benzamide;
N-[2-(3-Acetylamino-phenyl)-1H-pyrrolo[2,3-b]pyridin-5-yl]-2,4-dichloro-benzamide;
N-[2-(3-Acetylamino-phenyl)-1H-pyrrolo[2,3-b]pyridin-5-yl]-2-methoxy-benzamide;
N-[2-(3-Acetylamino-phenyl)-1H-pyrrolo[2,3-b]pyridin-5-yl]-2-chloro-6-methyl-benzamide; and N-[2-(3-Acetylamino-phenyl)-1H-pyrrolo[2,3-b]pyridin-5-yl]-2-chloro-5-methoxy-benzamide.

5. A compound according to claim 1, wherein:
$R^1$ is a phenyl group optionally substituted one to three, preferably one or two times with flourine, nitro, amino, —C(O)OH, heterocyclyl, —S(O)$_2$NH$_2$ or —X-alkyl; and the alkyl group is optionally substituted one or two times by hydroxy, alkoxy or dialkylamino;
X is —NR—, —O—, —S—, —S(O)$_2$—, —S(O)—, —NRC(O)— or —C(O)NR—;
R is hydrogen or alkyl, wherein the alkyl is optionally substituted one or two times by alkoxy;
$R^2$ and $R^3$ independently represent hydrogen, halogen, nitro, amino or alkyl;
$R^4$ is hydrogen; and
A is =N—.

6. A compound according to claim 5 selected from the group consisting of:
2-Chloro-N-(2-phenyl-3H-imidazo[4,5-b]pyridin-6-yl)-benzamide;
2-Chloro-6-methyl-N-(2-phenyl-3H-imidazo[4,5-b]pyridin-6-yl)-benzamide;
2-Bromo-N-(2-phenyl-3H-imidazo[4,5-b]pyridin-6-yl)-benzamide;
2-Methyl-5-nitro-N-(2-phenyl-3H-imidazo[4,5-b]pyridin-6-yl)-benzamide;
2-Chloro-5-nitro-N-(2-phenyl-3H-imidazo[4,5-b]pyridin-6-yl)-benzamide;
N-(2-Phenyl-3H-imidazo[4,5-b]pyridin-6-yl)-benzamide;
2-Chloro-N-{2-[3-(3-methoxy-propionylamino)-phenyl]-3H-imidazo[4,5-b]pyridin-6-yl}-benzamide;
5-Amino-2-methyl-N-(2-phenyl-3H-imidazo[4,5-b]pyridin-6-yl)-benzamide;
5-Amino-2-chloro-N-(2-phenyl-3H-imidazol[4,5-b]pyridin-6-yl)-benzamide;
2-Chloro-N-{2-[4-(2-diethylamino-ethoxy)-phenyl]-3H-imidazo[4,5-b]pyridin-6-yl}-benzamide;
2-Chloro-N-{2-[4-(2-methoxy-ethoxy)-phenyl]-3H-imidazo[4,5-b]pyridin-6-yl}-benzamide;
2-Chloro-N-{2-[3-(2-methoxy-ethoxy)-phenyl]-3H-imidazo[4,5-b]pyridin-6-yl}-benzamide;
2-Chloro-N-[2-(3-nitro-phenyl)-3H-imidazo[4,5-b]pyridin-6-yl]-benzamide;
2-Chloro-N-[2-(4-morpholin-4-yl-phenyl)-3H-imidazo[4,5-b]pyridin-6-yl]-benzamide;
2-Chloro-N-{2-[4-(4-methyl-piperazin-1-yl)-phenyl]-3H-imidazo[4,5-b]pyridin-6-yl}-benzamide;
2-Chloro-N-{2-[3-(2-hydroxy-ethyl)-phenyl]-3H-imidazo[4,5-b]pyridin-6-yl}-benzamide;
3-[6-(2-Chloro-benzoylamino)-3H-imidazo[4,5-b]pyridin-2-yl]-benzoic acid;
3-(6-(2-chlorobenzoylamino)-3H-imidazo[4,5-b]pyridin-2-yl)-N-(3-methoxy-propyl)-benzamide;
3-(6-(2-chlorobenzoylamino)-3H-imidazo[4,5-b]pyridin-2-yl)-N-isopropyl-benzamide;
2-Chloro-N-(2-{3-[2-methoxy-1-methoxymethyl-ethylcarbamoyl]-phenyl}-3H-imidazo[4,5-b]pyridin-6-yl)-benzamide;
2-Chloro-N-[2-(3-methylsulfanyl-phenyl)-3H-imidazo[4,5-b]pyridin-6-yl]-benzamide;
2-Chloro-N-[2-(4-sulfamoyl-phenyl)-3H-imidazo[4,5-b]pyridin-6-yl]-benzamide;
2-Chloro-N-[2-(4-nitro-phenyl)-3H-imidazo[4,5-b]pyridin-6-yl]-benzamide;
2-Chloro-N-[2-(4-methylsulfanyl-phenyl)-3H-imidazo[4,5-b]pyridin-6-yl]-benzamide;
2-Chloro-N-[2-(3-methanesulfinyl-phenyl)-3H-imidazo[4,5-b]pyridin-6-yl]-benzamide;
2-Chloro-N-[2-(4-methanesulfonyl-phenyl)-3H-imidazo[4,5-b]pyridin-6-yl]-benzamide;
N-[2-(3-Amino-phenyl)-3H-imidazo[4,5-b]pyridin-6-yl]-2-chloro-benzamide;
N-[2-(3-Acetylamino-phenyl)-3H-imidazo[4,5-b]pyridin-6-yl]-2-chloro-benzamide; and
N-(2-{4-[Bis-(2-methoxy-ethyl)-amino]-3-fluoro-phenyl}-3H-imidazo[4,5-b]pyridin-6-yl)-2-chloro-benzamide.

7. A compound according to claim 1, wherein:
$R^1$ is a heteroaryl group optionally substituted one or two times with heterocyclyl or —Z-alkyl; and the alkyl group is optionally substituted one or two times by alkoxy;
Z is a single bond or —NR—;
R is hydrogen;
$R^2$ and $R^3$ independently represent hydrogen or halogen;
$R^4$ is hydrogen; and
A is =N—.

8. A compound according to claim 7 selected from the group consisting of:
2-Chloro-N-(2-thiophen-2-yl-3H-imidazo[4,5-b]pyridin-6-yl)-benzamide;
2-Chloro-N-(2-thiophen-3-yl-3H-imidazo[4,5-b]pyridin-6-yl)-benzamide;
2-Chloro-N-[2-(2-methyl-pyridin-4-yl)-3H-imidazo[4,5-b]pyridin-6-yl]-benzamide;
2-Chloro-N-[2-(6-methyl-pyridin-3-yl)-3H-imidazo[4,5-b]pyridin-6-yl]-benzamide;
N-[2-(1H-Benzoimidazol-5-yl)-3H-imidazo[4,5-b]pyridin-6-yl]-2-chloro-benzamide;
2-Chloro-N-[2-(6-morpholin-4-yl-pyridin-3-yl)-3H-imidazo[4,5-b]pyridin-6-yl]-benzamide; and
2-Chloro-N-{2-[2-(3-methoxy-propylamino)-pyridin-4-yl]-3H-imidazo[4,5-b]pyridin-6-yl}-benzamide.

9. A process for the manufacture of a compound according to claim 1, wherein
(a) a compound of formula II,

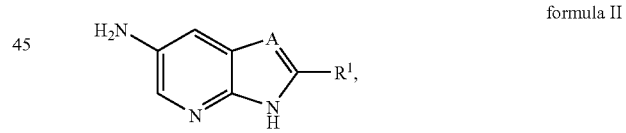

formula II wherein A and $R^1$ have the significance as given in formula I,
is reacted with a compound of formula III,

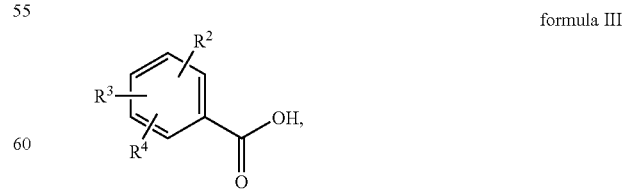

formula III wherein R, R and R have the significance given in formula I, and wherein the carboxylic acid group is activated before the reaction, to give the respective compound of formula I, (b) said compound of formula I is isolated from the reaction mixture, and
(c) if desired, converted into a pharmaceutically acceptable salt.

10. A pharmaceutical composition comprising a compound according to claim 1 and a pharmaceutically acceptable adjuvant.

11. A pharmaceutical composition according to claim 10 for the treatment of diseases mediated by an inappropriate activation of src family tyrosine kinases.

* * * * *